(12) United States Patent
Sambelashvili et al.

(10) Patent No.: US 8,204,590 B2
(45) Date of Patent: Jun. 19, 2012

(54) FUSION PACING INTERVAL DETERMINATION

(75) Inventors: Aleksandre T. Sambelashvili, Maple Grove, MN (US); Thomas J. Mullen, Andover, MN (US); Berthold Stegemann, Aachen (DE)

(73) Assignee: Medtronic, Inc., Minneapolis, MN (US)

( * ) Notice: Subject to any disclaimer, the term of this patent is extended or adjusted under 35 U.S.C. 154(b) by 666 days.

(21) Appl. No.: 12/363,025

(22) Filed: Jan. 30, 2009

(65) Prior Publication Data

US 2010/0198291 A1    Aug. 5, 2010

(51) Int. Cl.
*A61N 1/365* (2006.01)
(52) U.S. Cl. .......................................................... 607/9
(58) Field of Classification Search ............... 607/4, 5, 607/9, 14, 25
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel et al. | |
| 5,545,186 A | 8/1996 | Olson et al. | |
| 5,755,736 A | 5/1998 | Gillberg et al. | |
| 7,181,284 B2 | 2/2007 | Burnes et al. | |
| 2003/0083700 A1 | 5/2003 | Hill | |
| 2004/0172079 A1 | 9/2004 | Chinchoy | |
| 2005/0209648 A1 | 9/2005 | Burnes et al. | |
| 2006/0235478 A1 | 10/2006 | Van Gelder et al. | |
| 2007/0191891 A1 | 8/2007 | Burnes et al. | |
| 2008/0269823 A1 | 10/2008 | Burnes et al. | |

OTHER PUBLICATIONS

Lee et al., "Avoidance of Right Ventricular Pacing in Cardiac Resynchronization Therapy Improves Right Ventricular Hemodynamics in Heart Failure Patients", Journal of Cardiovascular Electrophysiology, vol. 18, No. 8, pp. 1-8, Aug. 2007.
(PCT/US2010/022536) PCT Notification of Transmittal of the International Search Report and the Written Opinion of the International Searching Authority.

*Primary Examiner* — Brian T Gedeon
(74) *Attorney, Agent, or Firm* — Carol F. Barry

(57) ABSTRACT

Delivery of fusion pacing therapy to a later depolarizing ventricle (V2) of a heart of a patient may be timed based on the depolarization of the V2 during at least one prior cardiac cycle. In some examples, a V2 pacing pulse is delivered upon the expiration of a pacing interval that begins at detection of an atrial sense or pace event ($A_{P/S}$). The pacing interval may be substantially equal to the duration of time between an $A_{P/S}$ and a V2 sensing event of at least one prior cardiac cycle decremented by an adjusted pre-excitation interval (PEI). In another example, the V2 pacing pulse is delivered at the expiration of a pacing interval that begins upon detection of a V2 sensing event of a prior cardiac cycle. The pacing interval may be substantially equal to a duration of time at least two subsequent V2 sensing events decremented by the adjusted PEI.

42 Claims, 11 Drawing Sheets

FUSION PACING INTERVAL DETERMINATION

TECHNICAL FIELD

The disclosure relates to implantable medical devices, and, more particularly, to cardiac therapy delivery by implantable medical devices.

BACKGROUND

Some types of implantable medical devices, such as cardiac pacemakers or implantable cardioverter defibrillators, provide therapeutic electrical stimulation to a heart of a patient via electrodes of one or more implantable leads. The therapeutic electrical stimulation may be delivered to the heart in the form of pulses or shocks for pacing, cardioversion or defibrillation. In some cases, an implantable medical device may sense intrinsic depolarizations of the heart, and control the delivery of therapeutic stimulation to the heart based on the sensing.

Cardiac resynchronization therapy is one type of therapy delivered by an implantable medical device. Cardiac resynchronization therapy may help enhance cardiac output by resynchronizing the electromechanical activity of the ventricles of the heart. Ventricular desynchrony may occur in patients that suffer from congestive heart failure (CHF).

SUMMARY

In general, the disclosure is directed to providing fusion-based cardiac resynchronization pacing therapy to a patient. The delivery of a pacing pulse to a later depolarizing ventricle (V2) is timed based on the depolarization of the V2 during at least one prior cardiac cycle, which may be detected by sensing an event in the V2 ($V2_S$) during the at least one prior cardiac cycle. The delivery of the V2 pacing pulse is timed such that the V2 is pre-excited and an evoked depolarization of the V2 is effected in fusion with the intrinsic depolarization of the first depolarizing ventricle (V1), resulting in a ventricular resynchronization.

In accordance with an example fusion pacing technique described herein, a V2 pacing pulse is delivered relative to an atrial sense or pace event ($A_{p/s}$). In one example, the V2 pacing pulse is delivered a predetermined period of time following the atrial sense or pace event ($A_{p/s}$), where the predetermined period of time (the "pacing interval") is substantially equal to the duration of time between an atrial event (sensed or paced) and a V2 sensing event ($V2_s$) of at least one prior cardiac cycle decremented by a time interval. In some examples, the time interval is predetermined by a clinician, while in other examples, the time interval is based on intrinsic conduction times determined by the clinician and/or a medical device. The time interval may be referred to as an adjusted pre-excitation interval (PEI). A PEI may be a function of the interval of time between the delivery of a V2 pacing pulse and a V1 sensing event, and may indicate the amount of time with which an V2 pulse precedes a V1 sensing event in order to achieve fusion of the electromechanical performance of the V1 and V2.

In some examples, an adjusted PEI is a function of the interval between a V1 sensing event and a V2 sensing event, and/or the interval between an atrial sense or pace event ($A_{P/S}$) and a V2 sensing event. For example, an adjusted PEI may be equal to an interval of time between a V1 sensing event and a V2 sensing event, incremented by the PEI. In other examples, the adjusted PEI may be a linear function that is based on intrinsic conduction times between an atrial pace or sensing event and a V1 sensing event, and the atrial pace or sensing event and a V2 sensing event.

In another example, the V2 pacing pulse is delivered a predetermined period of time (the "pacing interval") following a V2 sensing event of a prior cardiac cycle. The predetermined period of time is substantially equal to the duration of time between V2 sensing events ($V2_S$) of at least two consecutive prior cardiac cycles decremented by the adjusted pre-excitation interval (PEI).

In one aspect, the disclosure is directed to a method comprising detecting a ventricular sensing event of a ventricular chamber of a heart during at least a first cardiac cycle, and delivering pre-excitation fusion pacing therapy to the ventricular chamber during a second cardiac cycle that follows the first cardiac cycle, wherein the pre-excitation fusion pacing therapy is delivered upon expiration of a pacing interval that is determined based on the ventricular sensing event.

In another aspect, the disclosure is directed to a system comprising a stimulation generator that delivers pre-excitation fusion pacing therapy to a ventricular chamber of a heart, and a processor that detects a ventricular sensing event of the ventricular chamber during at least a first cardiac cycle and controls the stimulation generator to deliver the pre-excitation fusion pacing therapy to the ventricular chamber during a second cardiac cycle that follows the first cardiac cycle, wherein the processor controls the stimulation generator to time the delivery of the pre-excitation fusion pacing therapy upon expiration of a pacing interval that is determined based on the ventricular sensing event.

In another aspect, the disclosure is directed to a system comprising means for detecting a ventricular sensing event of a ventricular chamber of a heart during at least a first cardiac cycle, and means for delivering pre-excitation fusion pacing therapy to the ventricular chamber during a second cardiac cycle that follows the first cardiac cycle. The means for delivering pre-excitation fusion pacing therapy delivers the pacing therapy upon expiration of a pacing interval that is determined based on the ventricular sensing event.

In another aspect, the disclosure is directed to a computer-readable medium containing instructions. The instructions cause a programmable processor to detect a ventricular sensing event of a ventricular chamber of a heart during at least a first cardiac cycle, and control a stimulation generator to deliver pre-excitation fusion pacing therapy to the ventricular chamber during a second cardiac cycle that follows the first cardiac cycle. The pre-excitation fusion pacing therapy is delivered upon expiration of a pacing interval that is determined based on the ventricular sensing event.

In another aspect, the disclosure is directed to a computer-readable medium containing instructions. The instructions cause a programmable processor to perform any whole or part of the techniques described herein.

DETAILED DESCRIPTION

Figure 1:
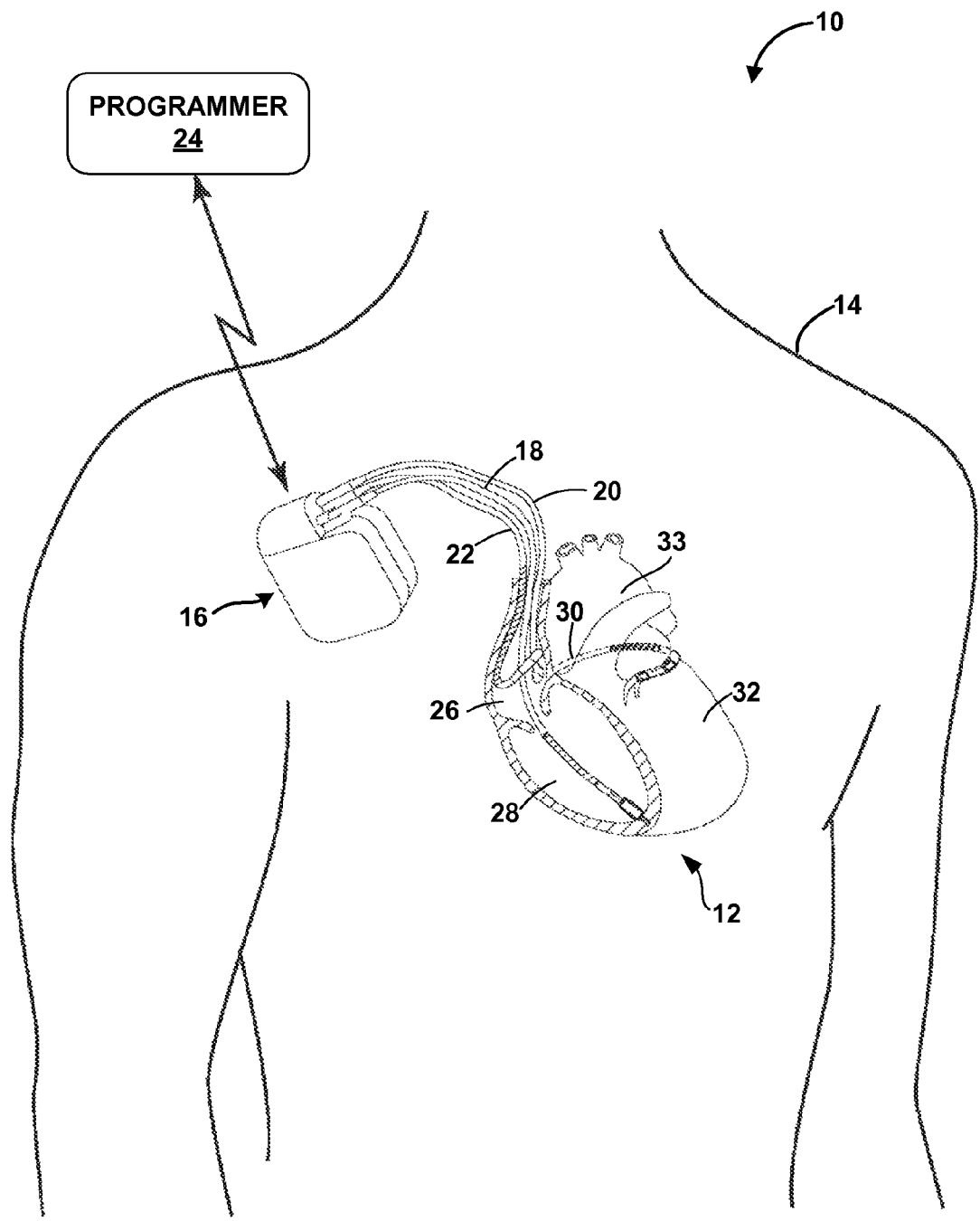
FIG. 1 is a conceptual diagram illustrating an example therapy system.

Devices, systems, and techniques for providing fusion-based cardiac resynchronization (CRT) pacing are described herein. Fusion-based cardiac resynchronization therapy is useful for restoring a depolarization sequence of a heart of a patient, which may be irregular due to ventricular dysfunction. As described herein, the timing of the delivery of a pacing pulse to a later depolarizing ventricle (V2) is based on a depolarization of the V2 in at least one prior cardiac cycle. The depolarization of the V2 may be detected by sensing an event in the V2 ($V2_S$), such as an R-wave of an electrical cardiac signal. The V2 pacing pulse ($V2_P$) is timed such that an evoked depolarization of the V2 is effected in fusion with the intrinsic depolarization of the first depolarizing ventricle (V1), resulting in a ventricular resynchronization. In this way, the V2 pacing pulse ($V2_P$) may pre-excite the conduction delayed V2 and help fuse the activation of the V2 with the activation of the V1 from intrinsic conduction. Thus, the pacing therapy described herein may be referred to as pre-excitation fusion pacing therapy. The interval of time between the V2 pacing pulse ($V2_P$) and the V2 sensing event ($V2_S$) of the same cardiac cycle may be referred to as the adjusted pre-excitation interval.

In some examples, the right ventricle (RV) may be the V1 and the left ventricle (LV) may be the V2. While the disclosure primarily refers examples in which the first depolarizing ventricle V1 is the RV and the later depolarizing ventricle V2 is the LV, the techniques described herein for providing fusion-based cardiac resynchronization therapy may also apply to examples in which the first depolarizing ventricle V1 is the LV and the later depolarizing ventricle V2 is the RV.

In existing fusion pacing techniques, the pacing pulse to the V2 ($V2_P$) is delivered upon expiration of a pacing interval that is determined based on the intrinsic depolarization of the V1. An example of an existing fusion pacing technique that times the delivery of the V2 pacing pulse ($V2_P$) to the intrinsic depolarization of the V1 is described in U.S. Pat. No. 7,181,284 to Burnes et al., which is entitled, "APPARATUS AND METHODS OF ENERGY EFFICIENT, ATRIAL-BASED BI-VENTRICULAR FUSION-PACING," and issued on Feb. 20, 2007. U.S. Pat. No. 7,181,284 to Burnes et al. is incorporated herein by reference in its entirety.

In one example provided by U.S. Pat. No. 7,181,284 to Burnes et al., a pacing pulse to the V2 ($V2_P$) is delivered a predetermined period of time following an atrial sense or pace event ($A_{P/S}$), where the predetermined period of time is substantially equal to the duration of time between the atrial sense or pace event ($A_{P/S}$) and a V1 sensing event ($V1_S$) of at least one prior cardiac cycle decremented by a duration of time referred to as the pre-excitation interval (PEI). The PEI may indicate the amount of time with which a V2 pulse precedes a V1 sensing event in order to achieve the fusing of the electromechanical performance of the V1 and V2. That is, the PEI may indicate the amount of time from the delivery of the V2 pacing pulse that is required to pre-excite the V2, such that the electromechanical performance of V1 and V2 merge into a fusion event. The PEI may be automatically determined by a medical device delivering the pacing therapy, e.g., based on determined intrinsic conduction times, or may be predetermined by a clinician.

While the existing timing techniques for the V2 pacing pulse ($V2_P$) are useful, the existing techniques require the use of a lead or a separate sensing device in the V1 in order to sense the V1 event (e.g., an R-wave sensed via electrodes in the first depolarizing ventricle V1). The techniques described herein may help eliminate the need for a separate lead and/or sensor in the V1 because the techniques described herein time the delivery of the V2 pacing pulse ($V2_P$) based on an event sensed in the V2, rather than the V1 as in existing systems. In this way, the techniques described herein may help minimize the invasiveness of a fusion pacing therapy system. In some examples, however, the systems and devices described herein may include a lead and/or sensor in both the V1 and V2. For example, the therapy systems described herein may be configured to provide back-up biventricular pacing via electrodes positioned within both the V1 and V2.

FIG. 1 is a conceptual diagram illustrating an example therapy system 10 that provides therapy to heart 12 of patient 14. Therapy system 10 includes IMD 16, which is coupled to leads 18, 20, and 22, and programmer 24. IMD 16 may be, for example, an implantable pacemaker that provides electrical signals to heart 12 and senses electrical activity of heart 12 via electrodes coupled to one or more of leads 18, 20, and 22. In some examples, IMD 16 may include cardioversion and/or defibrillation capabilities.

Leads 18, 20, 22 extend into the heart 12 of patient 14 to sense electrical activity of heart 12 and deliver electrical stimulation to heart 12. In the example shown in FIG. 1, right ventricular (RV) lead 18 extends through one or more veins (not shown), the superior vena cava (not shown), and right atrium (RA) 26, and into RV 28. Left ventricular (LV) coronary sinus lead 20 extends through one or more veins, the vena cava, right atrium 26, and into the coronary sinus 30 to a region adjacent to the free wall of LV 32 of heart 12. Right atrial (RA) lead 22 extends through one or more veins and the vena cava, and into the RA 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 may also sense electrical signals attendant to the depolarization and repolarization of heart 12 via extravascular electrodes (e.g., outside the vasculature of patient 14), such as epicardial electrodes, external surface electrodes, subcutaneous electrodes, and the like. In some examples, as described in further detail below, IMD 16 provides pacing pulses to heart 12 based on the electrical signals sensed within heart 12. For example, IMD 16 may provide pacing pulses to LV 32 based on the electrical signals sensed within LV 32. The configurations of electrodes used by IMD 16 for sensing and pacing may be unipolar or bipolar.

IMD 16 provides fusion-based cardiac resynchronization pacing therapy to heart 12. In particular, IMD 16 delivers a pacing stimulus (e.g., a pacing pulse) to LV 32 via electrodes of lead 20, where the pacing stimulus is timed such that an evoked depolarization of LV 32 is effected in fusion with the intrinsic depolarization of RV 28, resulting in a ventricular resynchronization. In this way, the pacing pulse delivered to LV 32 ($LV_P$) may pre-excite a conduction delayed LV 32 and help fuse the activation of LV 32 with the activation of RV 28 from intrinsic conduction. The fusion of the depolarization of LV 32 and RV 28 may result in synchronous activation and contraction of LV 32 with RV 28. As described in further detail below with reference to FIG. 6, IMD 16 times the delivery of the pacing pulse to LV 32 based on an LV 32 sensing event ($LV_S$) of at least one prior cardiac cycle. The prior cardiac cycle may be a cardiac cycle that precedes the current cardiac cycle in time, whereby the current cardiac cycle is the cycle for which IMD 16 delivers the LV 32 pacing therapy.

In some examples, IMD 16 delivers a single ventricular stimulus per cardiac cycle, although any suitable number of pacing stimuli per cardiac cycle is contemplated. As previously indicated, IMD 16 times the delivery of a LV pacing pulse ($LV_P$) with a LV sensing event ($LV_S$). In one example, IMD 16 delivers the LV pacing pulse ($LV_P$) a predetermined period of time following an atrial sense or pace event ($A_{P/S}$). This predetermined period of time may generally be referred to as a pacing interval. In this example, the predetermined period of time may also be referred to as the $A_{P/S}$–$LV_P$ interval or the $A_{P/S}$–$LV_P$ delay. The atrial pace or sensing event ($A_{P/S}$) may be a RA 26 pace or sensing event (e.g., a P-wave sensed via electrodes within RA 26 or a pacing pulse delivered to RA 26 via electrodes of lead 22) or a left atrium (LA) 33 pace or sensing event (e.g., a P-wave sensed via electrodes within LA 33 or a pacing pulse delivered to RA 26 via electrodes of lead 20).

In some examples, the predetermined period of time at which IMD 16 delivers the LV pacing pulse ($LV_P$) following an atrial sense or pace event ($A_{P/S}$) is substantially equal to the duration of time between an atrial event (sensed or paced) ($A_{P/S}$) and a LV 32 sensing event ($LV_S$) of at least one prior cardiac cycle decremented by a duration of time referred to as an adjusted PEI. That is, in some examples, the adjusted PEI indicates the desired interval of time between the delivery of the LV 32 pacing pulse ($LV_P$) and the LV 32 sensing event ($LV_S$) of the same cardiac cycle. In accordance with this example fusion pacing technique, the $A_{P/S}$–$LV_P$ delay is determined as follows:

$$A_{P/S}\text{–}LV_P\text{ delay}=(A_{P/S}\text{–}LV_S)\text{–adjusted PEI} \qquad \text{Equation (1):}$$

The duration of time between an atrial sense or pace event ($A_{P/S}$) and a LV 32 sensing event ($LV_S$) may be referred to as an atrioventricular (AV) delay. As previously indicated, a PEI may include the interval of time between the delivery of a LV pacing pulse ($LV_P$) and a RV sensing event ($RV_S$) of the same cardiac cycle that produces ventricular synchrony. The adjusted PEI may indicate an interval of time prior to an LV sensing event ($LV_S$) at which it may be desirable to deliver the LV pacing pulse ($LV_P$) in order to preexcite LV and merge the electromechanical performance of LV 32 and RV 28 into a fusion event. In some examples, an adjusted PEI is a linear function that is based on RV sensing event ($RV_S$) and a LV sensing event ($LV_S$) of the same cardiac cycle. For example, adjusted PEI may be determined as follows:

$$\text{Adjusted PEI}=a(RV_S\text{–}LV_S)+b \qquad \text{Equation (2):}$$

In Equation (2), the coefficients "a" and "b" may be fixed, empiric coefficients that are selected by a clinician or determined based on an adjusted PEI value selected by a clinician. In some examples, the coefficient "a" in Equation (2) may be about 1 and the coefficient "b" may be substantially equal to the PEI. In this case, the adjusted PEI is substantially equal to a time interval between an RV sensing event ($RV_S$) and a LV sensing event ($LV_S$) of the same cardiac cycle, incremented by the PEI. As a result, the $A_{P/S}$–$LV_P$ delay for timing the delivery of a LV pacing pulse may be determined as follows $$A_{P/S}\text{–}LV_P\text{ delay}=(A_{P/S}\text{–}LV_S)\text{–}[(RV_S\text{–}LV_S)+\text{PEI}] \qquad \text{Equation (3):}$$

Other values for the "a" and "b" coefficients in Equation (2) may be selected.

The magnitude of the PEI may differ based on various factors, such as the heart rate of patient 14, a dynamic physiologic conduction status of heart 12, which may changed based upon the physiological condition of patient 14 (e.g., ischemia status, myocardial infarction status, and so forth), as well as factors related to therapy system 10, such as the location of sensing electrodes of leads 18, 20, 22, location of pacing electrodes of lead 20, and internal circuitry processing delays of IMD 16. In some examples, the PEI may be preprogrammed into IMD 16 and specific to patient 14 or may be general to more patients. In some examples, the PEI may be in a range of about one millisecond (ms) to about 250 ms or more, such as about 100 ms to about 200 ms. The PEI may be fixed for at least a portion of time in which IMD 16 delivers fusion pacing therapy to patient 14, and a clinician or IMD 16 may periodically update PEI. In some cases, IMD 16 may store a plurality of PEI values and may automatically select a PEI value based on a physiological parameter value of patient 14, such as a heart rate.

The duration between an RV sensing event ($RV_S$) and a LV sensing event ($LV_S$) of the same cardiac cycle may be referred to as the interventricular conduction delay or the $RV_S$–$LV_S$ delay. The interventricular conduction delay, which may be used to determine the adjusted PEI, may be programmed into IMD 16 by a clinician. In some examples, the interventricular conduction delay may be relatively constant for patient 14 or undergo relatively slow changes. For example, the interventricular conduction delay (i.e., $RV_S$–$LV_S$) may remain substantially constant for a particular patient 14 for about three months to about six months, although the exact range of time for the constant interventricular conduction delay may vary based on the patient. Due to the relative slow changing nature of the interventricular conduction delay, the clinician may program the interventricular conduction delay into IMD 16 and periodically update the stored interventricular conduction delay value.

In other examples in which an adjusted PEI is a linear function that is based on RV sensing event ($RV_S$) and a LV sensing event ($LV_S$) of the same cardiac cycle, adjusted PEI may be determined based on the conduction times of heart 12. For example, in one example, adjusted PEI may be determined according to the following equation:

$$\text{Adjusted PEI}=c(A_{P/S}\text{–}RV_S)+d(A_{P/S}\text{–}LV_S)+e \qquad \text{Equation (4):}$$

In Equation (4), the coefficients "c", "d", and "e" may be fixed, empiric coefficients that are selected by a clinician or determined based on an adjusted PEI value selected by a clinician. In some examples, the coefficient "c" in Equation (4) may be about 0.3 to about 0.6, such as about 0.5 and the coefficient "d" may be about 0.3 to about 0.6, such as about 0.5, and the coefficient "e" may b about 40 to about 55, such as about 45. Other values for the "c", "d", and "e" coefficients in Equation (4) may be selected. In those cases, the $A_{P/S}$–$LV_P$ delay may be determined to be other values that are based on the A–$RV_S$ delay ($A_{P/S}$–$RV_S$) and the A–$LV_S$ delay ($A_{P/S}$–$LV_S$) of the same cardiac cycle.

In another example of a fusion pacing technique described herein, IMD 16 delivers the LV 32 pacing pulse ($LV_P$) after expiration of a pacing interval that begins upon detection of an LV 32 sensing event ($LV_S$) of an immediately preceding cardiac cycle. That is, IMD 16 delivers the LV 32 pacing pulse ($LV_P$) a predetermined period of time following an LV 32 sensing event ($LV_S$) of a prior cardiac cycle. In this example, the pacing interval is referred to as the $LV_S$–$LV_P$ interval or the $LV_S$–$LV_P$ delay. In some examples, the $LV_S$–$LV_P$ interval or the $LV_S$–$LV_P$ delay is substantially equal to the duration of time between LV 32 sensing events ($LV_S$) of at least two prior cardiac cycles decremented by the adjusted PEI. The duration of time between LV 32 sensing events ($LV_S$) of at least two prior cardiac cycles may be referred to as the $LV_S$–$LV_S$ delay. In accordance with this example fusion pacing technique, the $LV_S$–$LV_P$ delay may be determined as follows:

$$LV_S\text{-}LV_P \text{ delay}=(LV_S\text{-}LV_S)-\text{adjusted PEI} \quad \text{Equation (5):}$$

In Equation (5), adjusted PEI may be determined, e.g., using Equations (2) and (4) provided above, or based on the following equation:

$$\text{Adjusted PEI}=f*(LV_S\text{-}LV_S)+g \quad \text{Equation (6):}$$

In Equation (6), the coefficients "f" and "g" may be fixed, empiric coefficients that are selected by a clinician or determined based on an adjusted PEI value selected by a clinician. In some examples, the coefficient "f" in Equation (6) may be about 0.5 and the coefficient "g" may about 0 to about 10, although other coefficient values are contemplated. In accordance with Equations (5) and (6), the $LV_S$–$LV_P$ delay may be determined based on the $LV_S$–$LV_S$ delay for a prior cardiac cycle.

By timing the delivery of an LV pacing pulse ($LV_P$) based on the interventricular conduction delay and the sensed LV event ($LV_S$) using the Equations (1) and (5), IMD 16 may help maintain electrical fusion between RV 28 and LV 32, despite changes in the intrinsic A–$RV_S$ interval.

The fusion-based cardiac resynchronization therapy provided by IMD 16 may be useful for maintaining the cardiac rhythm in patient 14 with a conduction dysfunction, which may result when the natural electrical activation system of heart 12 is disrupted. The natural electrical activation system of a human heart 12 involves several sequential conduction pathways starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and a final distribution to the distal myocardial terminals via the Purkinje fiber network.

In a normal electrical activation sequence, the cardiac cycle commences with the generation of a depolarization wave at the SA Node in the wall of RA 26. The depolarization wave is transmitted through the atrial conduction pathways of Bachmann's Bundle and the Internodal Tracts at the atrial level into the LA 33 septum. When the atrial depolarization wave has reached the AV node, the atrial septum, and the furthest walls of the right and left atria 26, 33, respectively, the atria 26, 33 may contract as a result of the electrical activation. The aggregate right atrial and left atrial depolarization wave appears as the P-wave of the PQRST complex of an electrical cardiac signal, such as a cardiac electrogram (EGM) or electrocardiogram (ECG). When the amplitude of the atrial depolarization wave passing between a pair of unipolar or bipolar pace/sense electrodes located on or adjacent RA 26 and/or LA 33 exceeds a threshold, it is detected as a sensed P-wave. The sensed P-wave may also be referred to as an atrial sensing event, or an RA sensing event ($RA_S$). Similarly, a P-wave sensed in the LA 33 may be referred to as an atrial sensing event or an LA sensing event ($LA_S$).

During or after the atrial contractions, the AV node distributes the depolarization wave inferiorly down the Bundle of His in the intraventricular septum. The depolarization wave may travel to the apical region of heart 12 and then superiorly though the Purkinje Fiber network. The aggregate right ventricular and left ventricular depolarization wave and the subsequent T-wave accompanying re-polarization of the depolarized myocardium may appear as the QRST portion of the PQRST cardiac cycle complex. When the amplitude of the QRS ventricular depolarization wave passing between a bipolar or unipolar pace/sense electrode pair located on or adjacent RV 28 and/or LV 32 exceeds a threshold, it is detected as a sensed R-wave. The sensed R-wave may also be referred to as a ventricular sensing event, an RV sensing event ($RV_S$), or an LV sensing event ($LV_S$) depending upon which ventricle the electrodes of one or more of leads 18, 20, 22 are configured to sense in a particular case.

Some patients, such as patients with congestive heart failure or cardiomyopathies, may have left ventricular dysfunction, whereby the normal electrical activation sequence through heart 12 is compromised within LV 32. In a patient with left ventricular dysfunction, the normal electrical activation sequence through the heart of the patient becomes disrupted. For example, patients may experience an intra-atrial conduction defect, such as intra-atrial block. Intra-atrial block is a condition in which the atrial activation is delayed because of conduction delays between RA 26 to LA 33.

As another example, a patient with left ventricular dysfunction may experience an interventricular conduction defect, such as left bundle branch block (LBBB) and/or right bundle branch block (RBBB). In LBBB and RBBB, the activation signals are not conducted in a normal fashion along the right or left bundle branches respectively. Thus, in patients with bundle branch block, the activation of either RV 28 or LV 32 is delayed with respect to the other ventricle, causing asynchrony between the depolarization of the right and left ventricles. Ventricular asynchrony may be identified by a widened QRS complex due to the increased time for the activation to traverse the ventricular conduction paths. The asynchrony may result from conduction defects along the Bundle of His, the Right and Left Bundle Branches or at the more distal Purkinje Terminals. Typical intra-ventricular peak-to-peak asynchrony can range from about 80 ms to about 200 ms or longer. However, in patients who are experiencing RBBB and LBBB, the QRS complex may be widened far beyond the normal range to a wider range, e.g., about 120 ms to about 250 ms or greater.

Cardiac resynchronization therapy delivered by IMD 16 may help alleviate heart failure conditions by restoring synchronous depolarization and contraction of one or more chambers of heart 12. In some cases, the fusion pacing of heart 12 described herein enhances stroke volume of a patient by improving the synchrony with which RV 28 and LV 32 depolarize and contract.

IMD 16 may indefinitely deliver fusion-pacing therapy to heart 12 according to a determined pacing interval or for a limited period of time. The duration of a cardiac cycle of heart 12, which includes the depolarization-repolarization sequence, may change depending on various physiological factors of patient 14, such as a heart rate. As heart rate of patient 14 changes, the PEI that is used to determine the pacing interval and, therefore, time the delivery of a pacing pulse to LV 32 ($LV_P$) may change. Accordingly, it may be useful for IMD 16 to periodically evaluate the time delay with which a pacing pulse is delivered to heart 12 relative to an atrial pace or sensing event ($A_{P/S}$) or relative to a LV sensing event ($LV_S$) in order to maintain the delivery of the LV 32 pacing pulse ($LV_P$) at a time that results in a fusion of the depolarization of LV 32 and RV 28.

In some examples, IMD 16 delivers pacing pulses to LV 32 based on a particular pacing interval for a predetermined number of cardiac cycles occur or for a predetermined period of time. For example, after IMD 16 delivers pacing pulses to LV 32 for a predetermined number of cardiac cycles or for a predetermined period of time, IMD 16 may reevaluate the pacing interval and readjust the pacing interval as necessary. The number of cardiac cycles or predetermined period of time may be selected to be any clinically appropriate value and may be specific to patient 14 or general to more than one patient.

IMD 16 reevaluates the pacing interval in different ways, depending on the technique used to deliver the pacing therapy. For example, if the pacing interval is based on the interval of time between the atrial pace or sensing event ($A_{P/S}$) and an LV 32 sensing event ($LV_S$) (i.e., the $A_{P/S}$–$LV_S$ delay) using Equation (1) above, IMD 16 determines the current $A_{P/S}$–$LV_S$ delay. If the pacing interval is based on the interval of time between subsequent LV 32 sensing events ($LV_S$) (i.e., the $LV_S$–$LV_S$ delay) using Equation (5) above, IMD 16 determines the current $LV_S$–$LV_S$ delay. The determined $A_{P/S}$–$LV_S$ delay or the $LV_S$–$LV_S$ delay interval of time may be, for example, a mean or median of delays for multiple cardiac cycles or the respective delay for a single cardiac cycle. As described above, the $A_{P/S}$–$LV_S$ delay and the $LV_S$–$LV_S$ delay are used to determine the timing of a LV pacing pulse relative to the atrial pace or sensing event ($A_{P/S}$) or a LV sensing event ($LV_S$). IMD 16 may determine whether the $A_{P/S}$–$LV_S$ delay or the $LV_S$–$LV_S$ delay has changed, and, if so, modify the timing relative to the atrial pace or sensing event ($A_{P/S}$) or a LV sensing event ($LV_S$) with which the pacing pulse is delivered to LV 32.

In other examples, IMD 16 delivers pacing pulses to LV 32 until a loss of capture occurs in LV 32. If a loss of capture in the V2 chamber is detected it could indicate that the LV pacing pulse ($LV_P$) is being delivered too late (e.g., during the refractory period of LV 32) or that the LV 32 pacing electrodes have become dislodged or lead 20 has a lead-related condition (e.g., comprised insulation or a fracture). If the loss of capture is detected, e.g., by a failure to detect an LV sensing event ($LV_S$) following the delivery of a LV pacing pulse, IMD 16 may discontinue the pre-excitation pacing therapy. In some cases, IMD 16 switches to a different pacing mode (e.g., an AAI, ADI, AAI/R, ADI/R, double chamber DDD or DDD/R, and the like) after discontinuing the pre-excitation pacing therapy.

In some examples, IMD 16 also provides defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 is programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as sensed electrical activity, intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
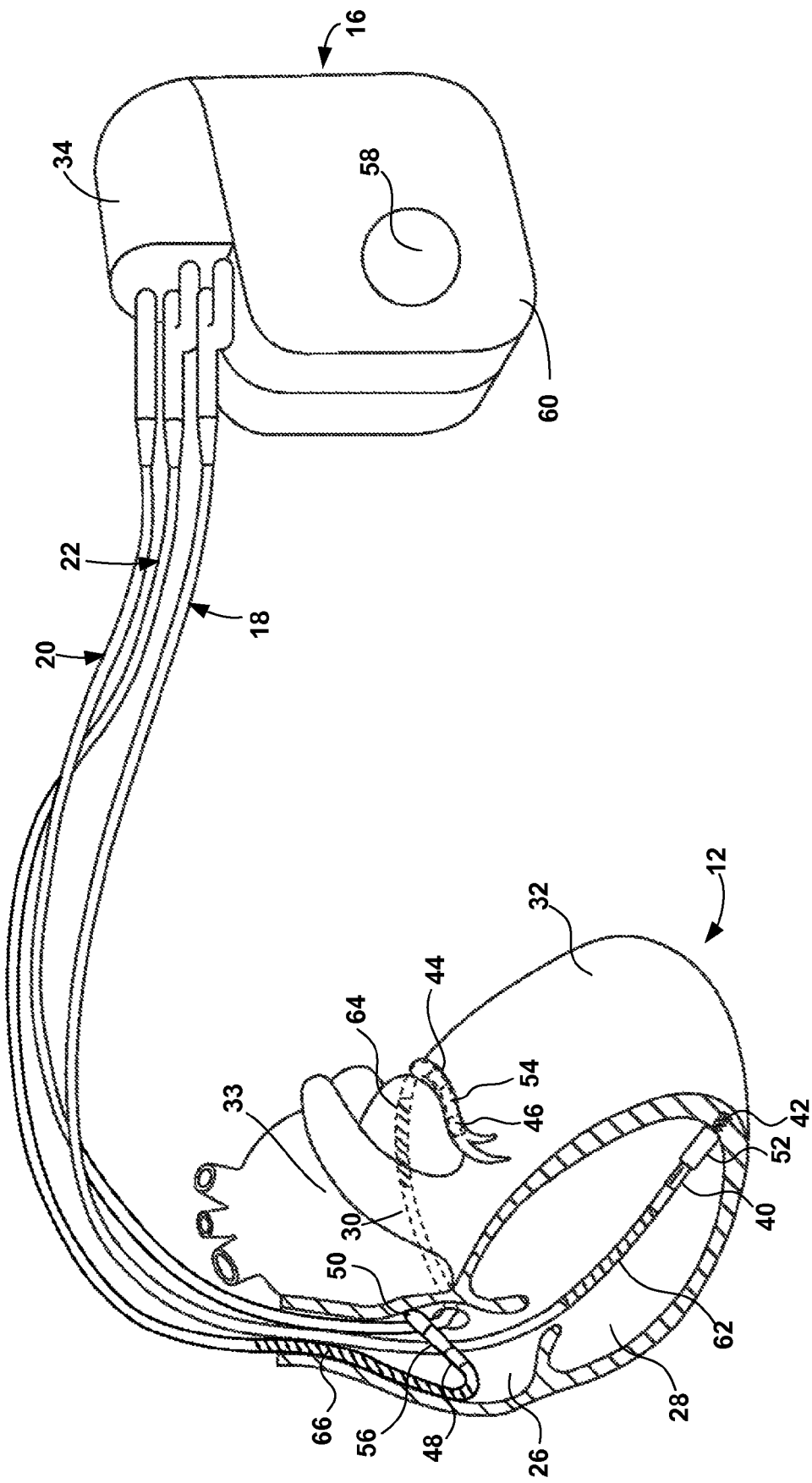
FIG. 2 is a conceptual diagram illustrating the medical device and leads of the therapy system of FIG. 1 in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules IMD 16 via connector block 34. In some examples, proximal ends of leads 18, 20, 22 include electrical contacts that electrically couple to respective electrical contacts within connector block 34. In addition, in some examples, leads 18, 20, 22 are mechanically coupled to connector block 34 with the aid of set screws, connection pins or another suitable mechanical coupling mechanism.

Each of the leads 18, 20, 22 includes an elongated insulative lead body, which may carry a number of conductors separated from one another by tubular insulative sheaths. In the illustrated example, bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. Electrodes 40, 44, and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses to LV 32 via electrodes 44, 46 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48, and 50 may be used for unipolar sensing or stimulation delivery in combination with housing electrode 58. As described in further detail with reference to FIG. 4, housing 60 may enclose a stimulation generator that generates cardiac pacing pulses and defibrillation or cardioversion shocks, as well as a sensing module for monitoring the patient's heart rhythm.

In some examples, leads 18, 20, 22 may also include elongated electrodes 62, 64, 66, respectively, which may take the form of a coil. IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include extravascular electrodes, such as subcutaneous electrodes, epicardial electrodes, and/or patch electrodes, instead of or in addition to the electrodes of transvenous leads 18, 20, 22 illustrated in FIG. 1. Further, IMD 16 need not be implanted within patient 14. In examples in which IMD 16 is not implanted in patient 14, IMD 16 may deliver defibrillation pulses, pacing pulses, and other therapies to heart 12 via percutaneous leads that extend through the skin of patient 14 to a variety of positions within or outside of heart 12.

Figure 3:
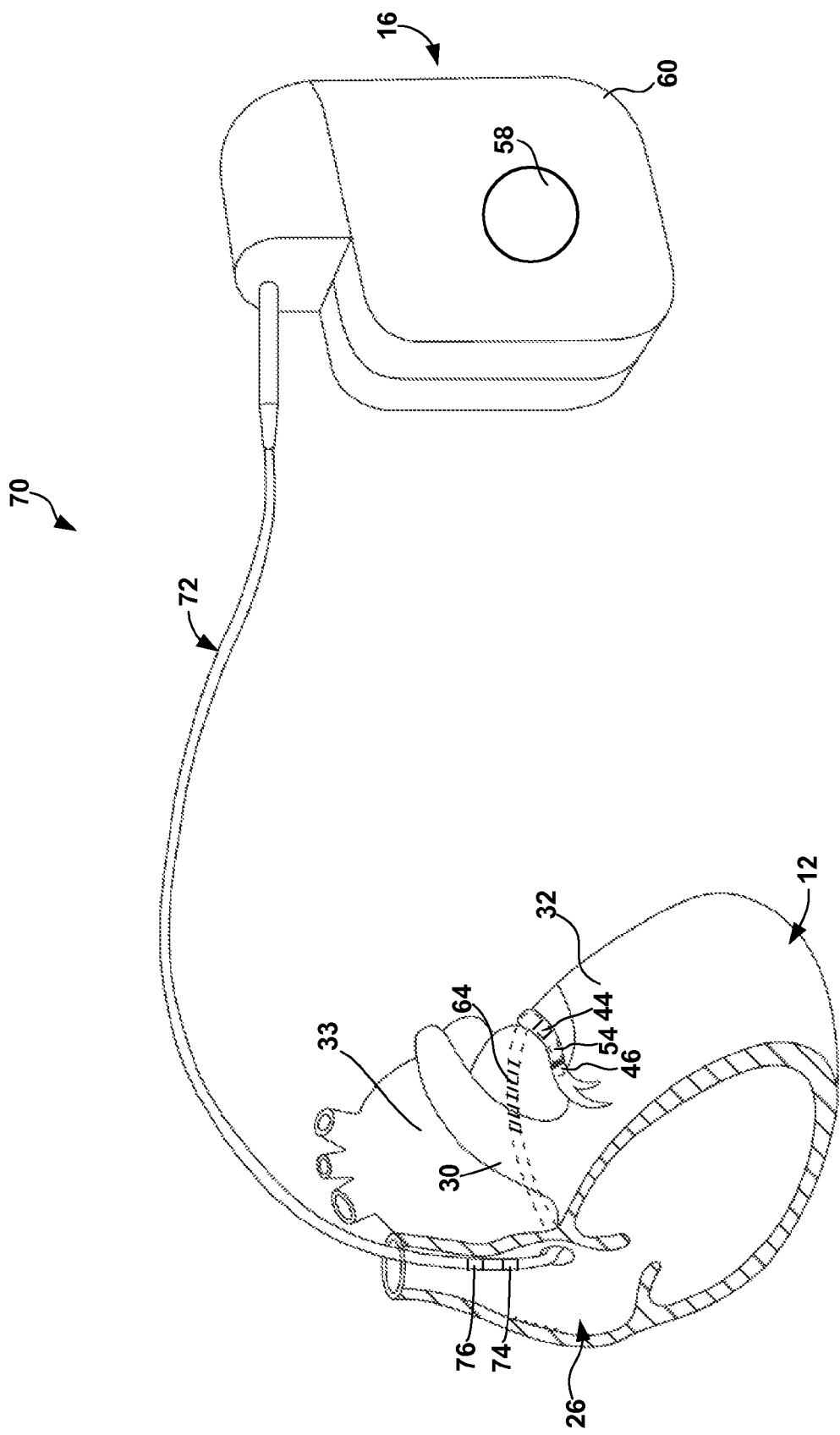
FIG. 3 is a conceptual diagram illustrating another example therapy system.

In other examples of therapy systems that provide electrical stimulation therapy to heart 12, a therapy system may include any suitable number of leads coupled to IMD 16, and each of the leads may extend to any location within or proximate to heart 12. For example, a therapy system may include a single chamber or dual chamber device rather than a three-chamber device as shown in FIG. 1. In a single chamber configuration, IMD 16 is electrically connected to a single lead 20 that includes stimulation and sense electrodes within LV 32. In one example of a dual chamber configuration, IMD 16 is electrically connected to a single lead that includes stimulation and sense electrodes within LV 32 as well as sense and/or stimulation electrodes within RA 26, as shown in FIG. 3. In another example of a dual chamber configuration, IMD 16 is connected to two leads that extend into a respective one of RA 28 and LV 32. Other lead configurations are contemplated.

FIG. 3 is a conceptual diagram illustrating another example therapy system 70, which is similar to therapy system 10 of FIGS. 1-2, but includes a single lead 72, rather than three leads. Lead 72 is implanted within LV 32 and RA 26. Lead 72 is similar to lead 20 of FIG. 2, but includes electrodes 74, 76 within RA 26 to sense electrical activity of RA 26 (e.g., P-waves). Therapy system 70 shown in FIG. 4 may be useful for providing pacing pulses to LV 32 of heart 12 in accordance with the fusion-based cardiac resynchronization techniques described herein. While the description of FIGS. 2-9 primarily refers to therapy system 10 of FIG. 2, the devices, systems, and techniques described herein may also be used to implement therapy delivery by therapy system 70.

Figure 4:
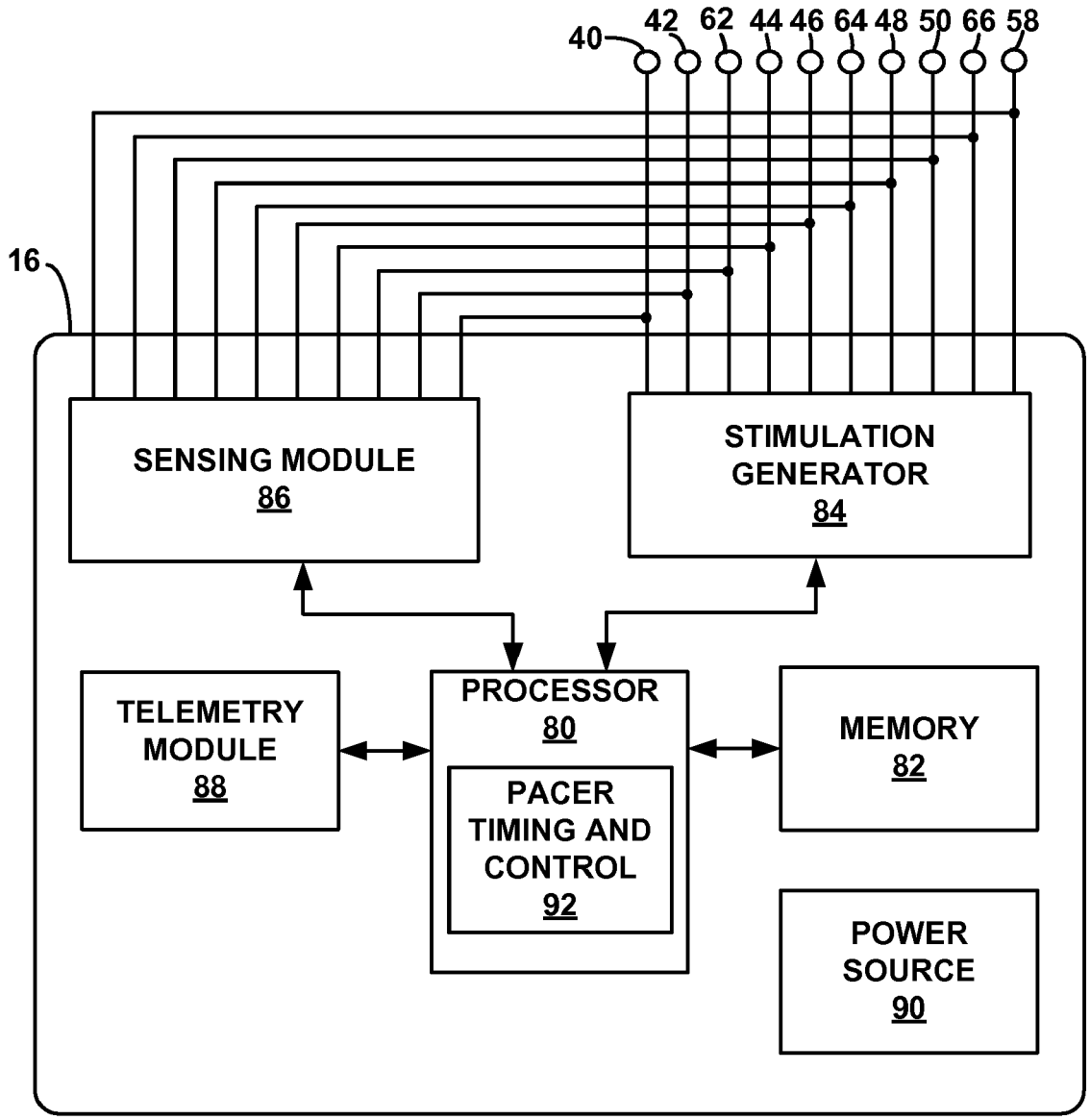
FIG. 4 is a functional block diagram of an example implantable medical device that delivers stimulation to a heart of a patient.

FIG. 4 is a functional block diagram of one example configuration of IMD 16, which includes processor 80, memory 82, stimulation generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. In addition to sensed physiological parameters of patient 14 (e.g., EGM or ECG signals), one or more PEI values and/or adjusted PEI values may be stored by memory 82. As discussed above, the PEI values may be associated with a heart rate or a range of heart rates, and processor 80 may select a PEI from memory 82 based on a detected heart rate.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 according to a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Stimulation generator 84 is configured to generate and deliver electrical stimulation therapy. For example, stimulation generator 84 may deliver a pacing stimulus to LV 32 (FIG. 2) of heart 12 in accordance with the fusion pacing techniques described herein heart 12 via at least two electrodes 44, 46 (FIG. 2). In some examples, stimulation generator 84 is configured to deliver cardioversion or defibrillation shocks to heart 12. The pacing stimuli, cardioversion shocks, and defibrillation shocks may be in the form of stimulation pulses. In other examples, stimulation generator may deliver one or more of these types of stimulation in the form of other signals, such as sine waves, square waves, or other substantially continuous time signals.

Stimulation generator 84 may include a switch module, and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12, e.g., via EGM signals. For example, sensing module 86 may sense atrial events (e.g., a P-wave) with electrodes 48, 50, 66 within RA 26 or sense an LV 32 event (e.g., an R-wave) with electrodes 44, 46, 64 within LV 32. Sensing module 86 may include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprises an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in RV 28 of heart 12. Another channel may include another R-wave amplifier that receives signals from electrodes 44 and 46, which are used for pacing and sensing proximate to LV 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in RA 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

Processor 80 may define variable intervals for timing the delivery of LV fusion pacing pulses ($LV_P$) based on signals from sensing module 86. These intervals may include, for example, the pacing interval (e.g., $A_{P/S}$–$LV_P$ delay or $LV_S$–$LV_P$ delay) and intervals used to determined the pacing interval (e.g., $A_{P/S}$–$LV_S$, $RV_S$–$LV_S$, or $LV_S$–$LV_S$). Signals generated by sensing module 86 may include, for example: an RA-event signal, which indicates a detection of a P-wave via electrodes implanted within RA 26 (FIG. 1); an LA-event signal, which indicates a detection of a P-wave via electrodes implanted within LA 33 (FIG. 1); an RV-event signal, which indicates a detection of an R-wave via electrodes implanted within RV 28; or an LV-event signal, which indicates a detection of an R-wave via electrodes implanted within LV 32. In the example of therapy systems 10, 70 shown in FIGS. 2 and 3, IMD 16 is not connected to electrodes that are implanted within LA 33. However, in other example therapy systems, IMD 16 may be connected to electrodes that are implanted within LA 33 in order to sense electrical activity of LA 33.

An example of a pacing interval processor 80 may define based on these different types of signals generated by sensing module 86 is the interval of time following an atrial sense or pacing event ($A_{P/S}$) at which the pacing pulse is delivered to LV 32. As described above, this interval may be referred to as the $A_{P/S}$–$LV_P$ interval or the $A_{P/S}$–$LV_P$ delay. An example technique for determining the $A_{P/S}$–$LV_P$ delay is described with reference to FIG. 6. As another example, processor 80 may define the AV delay, which may include the time period between an atrial sense or pace event ($A_{P/S}$) and a LV 32 sensing event ($LV_S$). Processor 80 may, for example, determine the AV delay to be the time interval between a sensed P-wave and an R-wave sensed via lead 20 (FIG. 2) implanted within LV 32.

In some examples, processor 90 defines the pacing interval that is substantially equal to the interval of time following a LV 32 sensing event ($LV_S$) at which the pacing pulse ($LV_P$) is delivered to LV 32. As described above, this interval may be referred to as the $LV_S$–$LV_P$ interval or the $LV_S$–$LV_P$ delay. An example technique for determining the $LV_S$–$LV_P$ delay is described with reference to FIG. 10. In addition, processor 80 may define the $LV_S$–$LV_S$ interval, which is the interval of time between subsequent LV 32 sensing events ($LV_S$) that may be used for Equation (5) above. Processor 80 may, for example, determine the $LV_S$–$LV_S$ interval to be the time interval between subsequent R-waves sensed via lead 20 (FIG. 2) implanted within LV 32. Processor 80 may also define the $RV_S$–$LV_S$ interval, which may be used to determine the adjusted PEI. For example, processor 80 may determine the $RV_S$–$LV_S$ interval to be the time interval between an R-wave sensed via lead 18 (FIG. 2) implanted within RV 28 and an R-wave of the same cardiac cycle sensed via lead 20 (FIG. 2) implanted within LV 32.

Processor 80 includes pacer timing and control module 92, which may be embodied as hardware, firmware, software, or any combination thereof. Pacer timing and control module 92 may comprise a dedicated hardware circuit, such as an ASIC, separate from other processor 80 components, such as a microprocessor, or a software module executed by a component of processor 80 (e.g., a microprocessor or ASIC). Pacer timing and control module 92 may help define the pacing interval (e.g., $A_{P/S}$–$LV_P$ delay and/or the $LV_S$–$LV_P$ delay) for controlling the delivery of a pacing pulse to LV 32. For example, pacing timing and control module 92 may include programmable counters or timers for determining the $A_{P/S}$–$LV_P$ delay, the $LV_S$–$LV_P$ delay, and/or any other relevant time intervals. In addition, pacing timing and control module 92 may include timers for timing the delivery of pacing pulses and other functions that are based on the pacing interval.

In examples in which IMD 16 delivers the LV pacing pulse ($LV_P$) a predetermined period of time following an atrial sense or pace event ($A_{P/S}$), pacing timing and control module 92 may include a timer that is loaded with the appropriate $A_{P/S}$–$LV_P$ delay. The timer of pacing timing and control module 92 may be configured to begin upon the detection of a preceding atrial pace or sensing event ($A_{P/S}$). Upon expiration of the particular timer, processor 80 may control stimulation generator 84 to deliver pacing stimulus $LV_P$ to LV 32 (FIG. 1). For example, pacing timing and control module 92 may generate a trigger signal that triggers the output of a pacing pulse by stimulation generator 84.

In examples in which IMD 16 delivers the LV pacing pulse ($LV_P$) a predetermined period of time following a LV sensing event ($LV_S$), pacing timing and control module 92 may include a timer that is loaded with the appropriate $LV_S$–$LV_P$ delay. The timer of pacing timing and control module 92 may be configured to begin upon detection of a preceding atrial pace or sensing event ($LV_S$). Upon expiration of the particular timer, processor 80 may control stimulation generator 84 to deliver pacing stimulus $LV_P$ to LV 32 (FIG. 1).

In examples in which IMD 16 is configured to deliver other types of cardiac rhythm therapy in addition to pre-excitation fusion pacing, pacer timing and control module 92 may also include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

In examples in which IMD 16 is configured to deliver other types of cardiac rhythm therapy in addition to excitation fusion pacing, intervals defined by pacer timing and control module 92 within processor 80 may include atrial and ventricular pacing escape intervals, refractory periods during which sensed P-waves and R-waves are ineffective to restart timing of the escape intervals, and the pulse widths of the pacing pulses. As another example, pacer timing and control module 92 may define a blanking period, and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing modes other than the fusion-based pacing, escape interval counters within pacer timing/control module 92 of processor 80 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including fusion-based cardiac resynchronization therapy.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as ventricular fibrillation event or ventricular tachycardia event. Upon detecting a threshold number of tachyarrhythmia events, processor 80 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode.

In some examples, processor 80 may operate as an interrupt driven device, and is responsive to interrupts from pacer timing and control module 92, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 80 in other examples.

In the examples described herein, processor 80 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 82 of IMD 16. In addition, the number of tachyarrhythmia events that are detected to confirm the presence of a tachyarrhythmia episode may be stored as a number of intervals to detect (NID) threshold value in memory 82. In some examples, processor 80 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 80 may determine that the tachyarrhythmia is present.

If processor 80 detects an atrial or ventricular tachyarrhythmia based on signals from sensing module 86, and an anti-tachyarrhythmia pacing regimen is desired, processor 80 may load timing intervals for controlling the generation of anti-tachyarrhythmia pacing therapies by stimulation generator 84 into pacer timing and control module 92 to control the operation of the escape interval counters therein and to define refractory periods during which detection of R-waves and P-waves is ineffective to restart the escape interval counters.

If IMD 16 is configured to generate and deliver defibrillation pulses to heart 12, stimulation generator 84 may include a high voltage charge circuit and a high voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module (not shown), which may, like pacer timing and control module 92, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of stimulation generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., EGM signals) produced by atrial and ventricular sense amp circuits within sensing module 86 to programmer 24. Other types of information may also be transmitted to programmer 24, such as the various intervals and delays used to deliver the fusion pacing pulse to LV 32. Programmer 24 may interrogate IMD 16 to receive the heart signals. Processor 80 may store heart signals within memory 82, and retrieve stored heart signals from memory 82. Processor 80 may also generate and store marker codes indicative of different cardiac episodes that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

Figure 5:
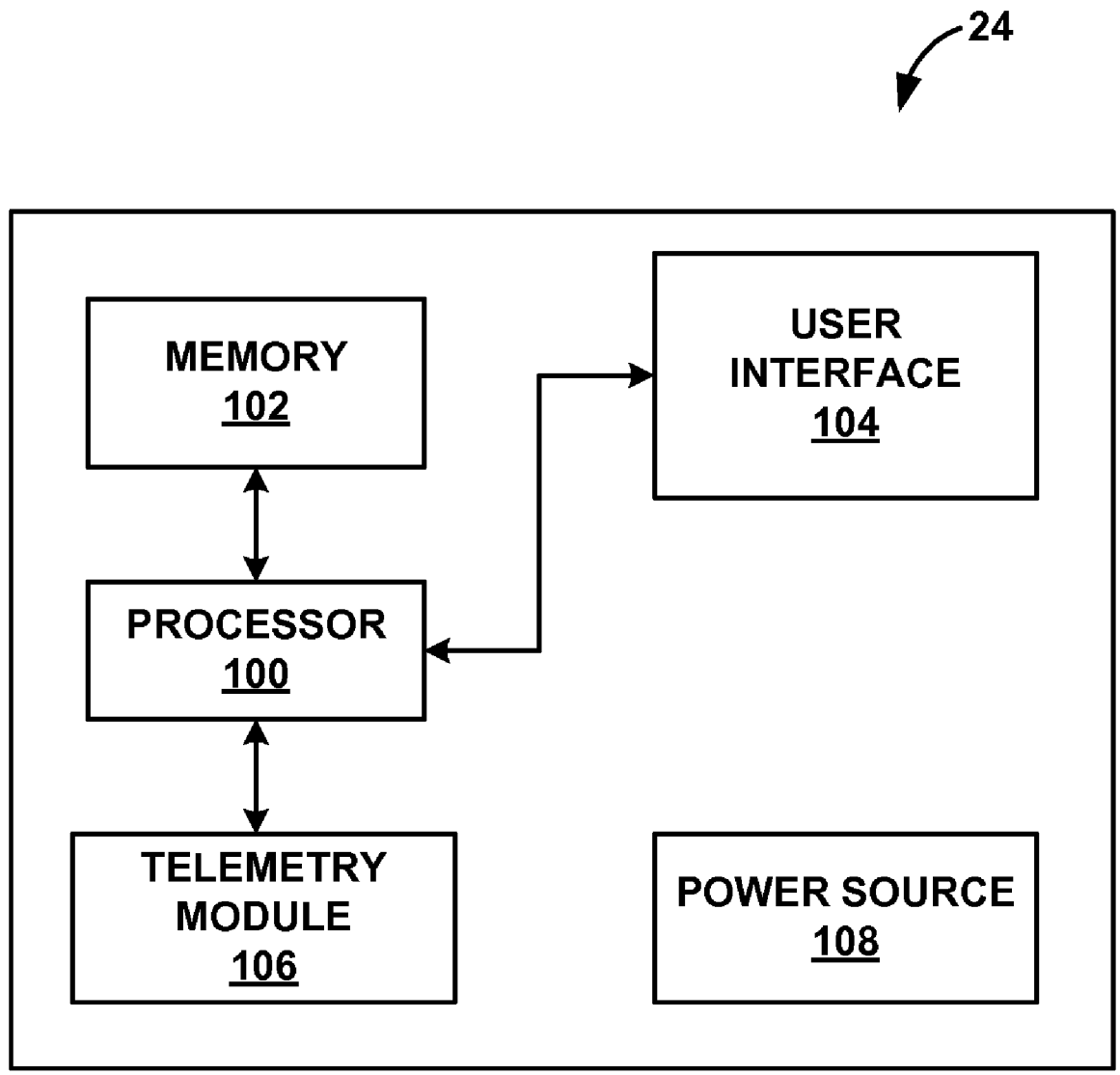
FIG. 5 is a functional block diagram of an example medical device programmer.

FIG. 5 is block diagram of an example programmer 24. As shown in FIG. 5, programmer 24 includes processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 102 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1.

Telemetry module 106 may be similar to telemetry module 88 of IMD 16 (FIG. 4). Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 104 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Example techniques that IMD 16 may implement in order to deliver fusion-based cardiac resynchronization therapy to patient 14 are described with respect to FIGS. 6-9. FIGS. 6-9 describe techniques for timing the delivery of a LV pacing pulse with an LV sensing event in order to achieve electromechanical fusion with the corresponding intrinsic depolarization of RV 28 (FIG. 1). However, for patients with RV conduction dysfunction, the example techniques described with respect to FIGS. 6-9 may also be used to time the delivery of an RV pacing pulse with an RV sensing event in order to achieve electromechanical fusion with the corresponding intrinsic depolarization of LV 32 (FIG. 1).

Figure 6:
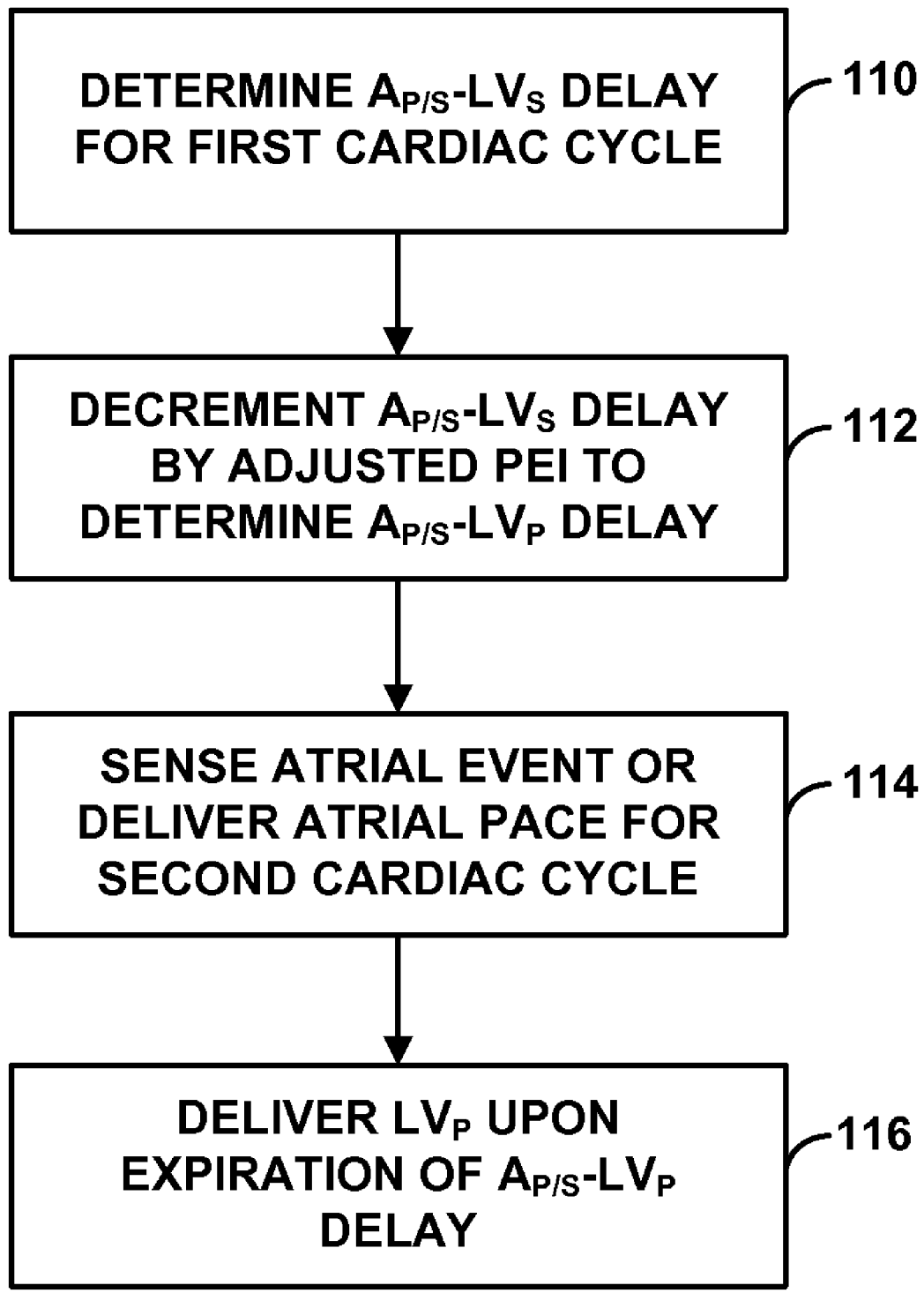
FIGS. 6-8 are flow diagrams of example techniques for providing fusion-based cardiac resynchronization therapy.

FIG. 6 is a flow diagram of an example technique for providing fusion-based cardiac resynchronization therapy to patient 14 according to a pacing interval that is based on a LV sensing event. In the technique shown in FIG. 6, processor 80 (FIG. 4) of IMD 16 controls the delivery of a pacing pulse $LV_P$ to LV 32 (FIG. 2) relative to an atrial pace or sensing event ($A_{P/S}$). In particular, processor 80 may implement the technique shown in FIG. 6 to determine an $A_{P/S}$–$LV_P$ delay, which is one type of pacing interval, for delivering the LV pacing stimulus to heart 12.

In accordance with the technique shown in FIG. 6, processor 80 determines the $A_{P/S}$–$LV_S$ delay for a first cardiac cycle of patient 14, which is the interval of time between an atrial sensing event (e.g., a P-wave of a sensed EGM) or an atrial pacing stimulus delivered by IMD 16 and an LV sensing event (e.g., an R-wave of a sensed EGM) (110). The atrial sensing event and the LV sensing event may be detected based on signals generated by sensing module 86 of IMD 16, as discussed above with respect to FIG. 4. Processor 80 decrements the determined $A_{P/S}$–$LV_S$ delay by an adjusted PEI value to determine an $A_{P/S}$–$LV_P$ delay (112). In this example, the pacing interval, $A_{P/S}$–$LV_P$ interval, indicates the period of time following an atrial sensing event or an atrial pace at which processor 80 controls stimulation generator 84 to deliver a pacing stimulus to LV 32. The adjusted PEI may be stored in memory 82 (FIG. 4) of IMD 16 or determined based on, e.g., Equations (2), (4), and (6) above. Technique for determining the adjusted PEI are described with respect to FIGS. 9A and 9B.

After determining the $A_{P/S}$–$LV_P$ interval (112), processor 80 may detect an atrial sensing event or an atrial pace (114). For example, processor 80 may receive an atrial sensing event signal from sensing module 86 (FIG. 2) or control stimulation generator 84 to deliver an atrial pace to either RA 26 or LA 33 (114). The atrial event may be an atrial event of a second cardiac cycle that is subsequent to the first cardiac cycle. Similarly, the atrial pace may be a pacing stimulus that is delivered to RA 26 or RA 33 during a second cardiac cycle that follows the first cardiac cycle. In some examples, the second cardiac cycle may immediately follow the first cardiac cycle.

Processor 80 controls stimulation generator 84 to deliver a pacing stimulus $LV_P$ (e.g., one or more pacing pulses) to LV 32 of heart 12 after the $A_{P/S}$–$LV_P$ interval of time following the sensed atrial event or atrial pace (116). Timing the delivery of the LV pacing pulse ($LV_P$) based on the adjusted PEI and the LV sensing event ($LV_S$) may help pre-excite LV 32 of heart 12 such that LV 32, which may suffer from a conduction dysfunction (e.g., a conduction block), may depolarize in synchrony with RV 28, which may depolarize intrinsically. In some examples, pacer timing and control module 92 (FIG. 4) of processor 80 starts a timer upon the sensing of the atrial event or delivering of an atrial pulse during the second cardiac cycle (114), where the timer may have a duration of the $A_{P/S}$–$LV_P$ interval. Upon expiration of the timer, processor 80 controls stimulation generator 84 to deliver the LV pacing pulse ($LV_P$) (116).

Figure 7:
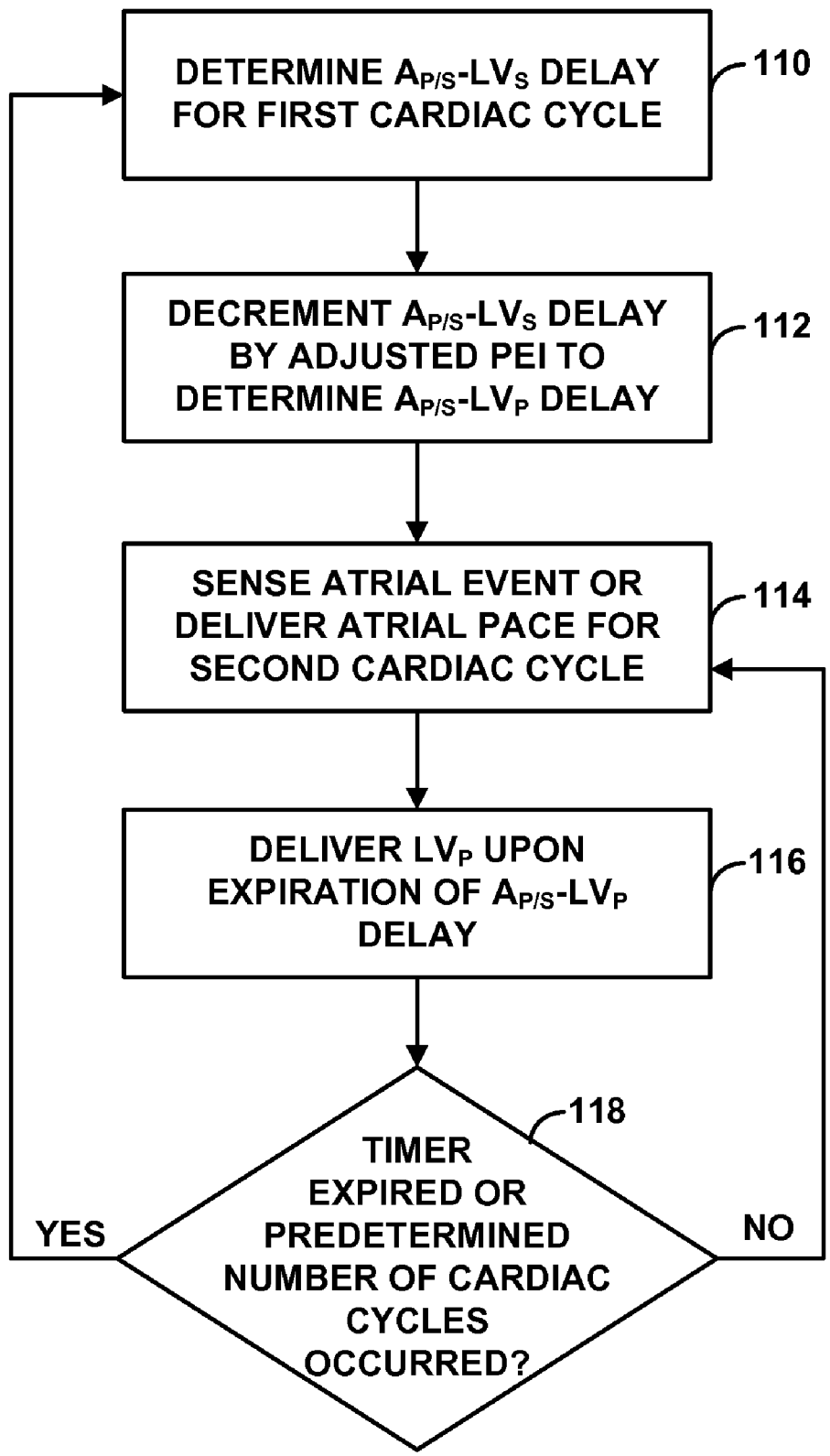

As previously indicated, in some examples, processor 80 may indefinitely sense an atrial event or atrial pulse (114) and control stimulation generator 84 to deliver the LV pacing pulse ($LV_P$) to heart 12 in accordance with the determined $A_{P/S}$–$LV_P$ delay. In other examples, processor 80 controls stimulation generator 84 to deliver the LV pacing pulse ($LV_P$) to heart 12 in accordance with the determined $A_{P/S}$–$LV_P$ for a limited period of time. FIG. 7 is a flow diagram of an example of such a technique. In the technique shown in FIG. 7, processor 80 determines the $A_{P/S}$–$LV_S$ delay (110) and determines the $A_{P/S}$–$LV_P$ delay (112). Processor 80 may then sense an atrial event or control stimulation generator 84 to deliver an atrial pacing stimulus (114) and control stimulation generator 84 (114) and deliver the LV pacing pulse ($LV_P$) to heart 12 upon expiration of the $A_{P/S}$–$LV_P$ delay (116).

After delivering the LV pacing pulse ($LV_P$) to heart 12, processor 80 determines whether a timer has expired or whether a predetermined number of cardiac cycles have occurred (118). The timer or the predetermined number of cardiac cycles may indicate the frequency with which processor determines the $A_{P/S}$–$LV_S$ delay. It may be desirable for processor 80 to periodically determine the $A_{P/S}$–$LV_S$ delay because the pacing interval, e.g., $A_{P/S}$–$LV_S$ delay, may change with the patient's heart rate or other physiological parameters.

In some examples, the timer has a duration of about 10 seconds to about 60 seconds, such as about 30 seconds. However, other durations of time are contemplated. In some examples, the predetermined number of cardiac cycles is in a range of about 10 cardiac cycles to about 60 cardiac cycles, although any threshold number of cardiac cycles are contemplated. Processor 80 may use any suitable technique to determine whether the timer has expired or whether the predetermined number of cardiac cycles has occurred. For example, processor 80 may utilize a counter to count the number of cardiac cycles. As another example, pacer timing and control module 92 (FIG. 4) of processor 80 may include a timer dedicated to determining when processor should modify the $A_{P/S}$–$LV_S$ delay.

If the timer has expired or the predetermined number of cardiac cycles have occurred (118), processor 80 determines the $A_{P/S}$–$LV_S$ delay (110) in order to re-determine the pacing interval, which is $A_{P/S}$–$LV_S$ delay in this example. On the other hand, if the timer has not expired or the predetermined number of cardiac cycles have not occurred, processor 80 continues sensing atrial events or delivering atrial pacing pulses (114) and controlling stimulation generator 84 (114)

and deliver the LV pacing pulse ($LV_P$) to heart 12 upon expiration of the most recently determined $A_{P/S}$–$LV_P$ delay (116).

Figure 8:
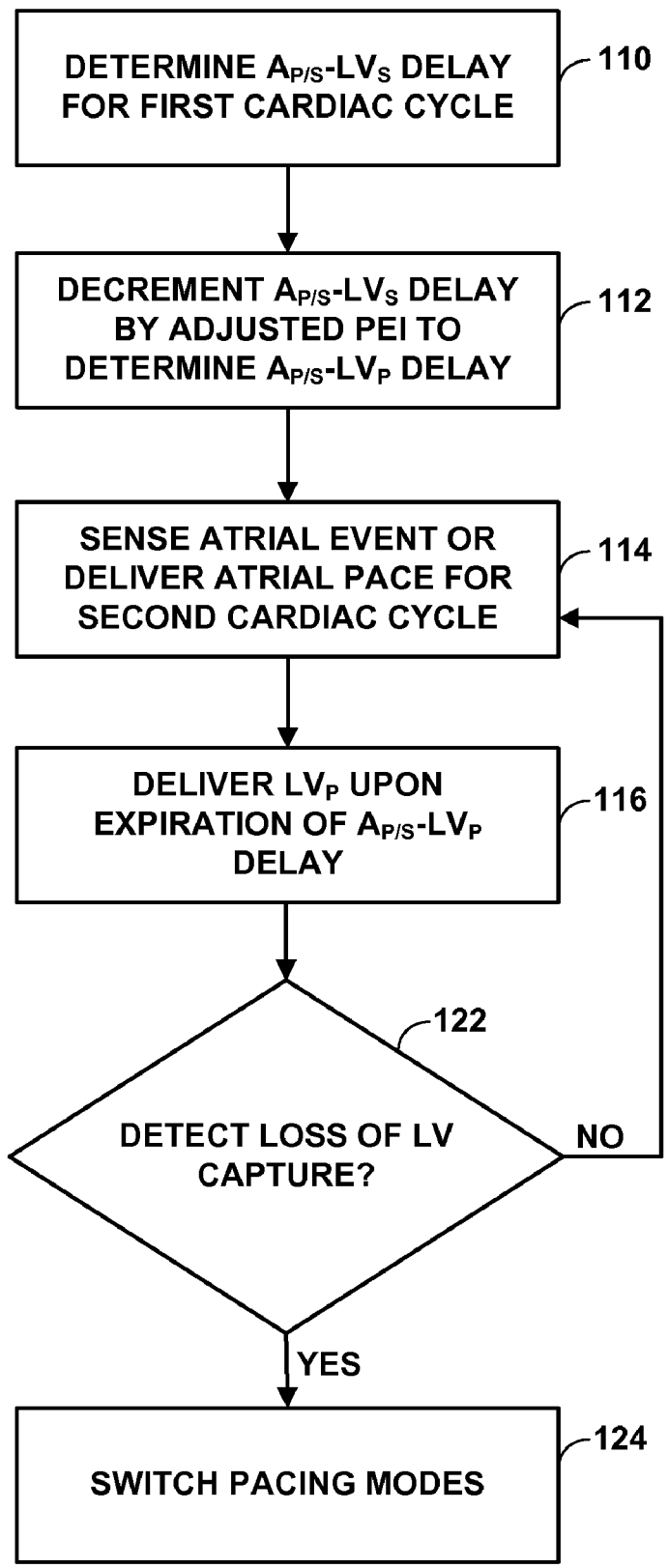

FIG. 8 is a flow diagram of an example technique in which processor 80 controls stimulation generator 84 to deliver the LV pacing pulse ($LV_P$) to heart 12 in accordance with the determined $A_{P/S}$–$LV_P$ until a loss of LV capture is detected. As with the technique shown in FIG. 6, in the technique shown in FIG. 8, processor 80 determines the $A_{P/S}$–$LV_S$ delay (110) and determines the pacing interval, which is the $A_{P/S}$–$LV_P$ delay in the example shown in FIG. 8 (112). Processor 80 may then sense an atrial event or control stimulation generator 84 to deliver an atrial pacing stimulus (114) and control stimulation generator 84 (114) and deliver the LV pacing pulse ($LV_P$) to heart 12 upon expiration of the $A_{P/S}$–$LV_P$ delay following the atrial sense or pace event (116).

Processor 80 periodically determines whether loss of LV 32 capture is detected (122). In the example shown in FIG. 8, processor 80 determines whether loss of LV 32 capture is detected after the delivery of each pacing stimulus to LV 32. Loss of LV 32 capture may indicate that the delivery of a pacing stimulus to LV 32 is ineffective. Loss of capture may be attributable to various causes. In some cases, lead 20 (FIG. 2) with which IMD 16 delivers a pacing stimulus to LV 32 may migrate, such that electrodes 44, 46 (FIG. 2) are no longer in contact with a wall of LV 32 or are otherwise decoupled from LV 32. In other cases, the delivery of a pacing stimulus to LV 32 may be compromised by a lead-related condition, which may include, for example, a change in the structure of at least a part of the lead. For example, a conductor within lead 20 may fracture or electrical insulation of one of the conductors within the lead may change, thereby causing conductors to contact one another or with body fluids and resulting in a low impedance or a short circuit. In other cases, a lead conductor may fracture and exhibit an intermittent or continuous open circuit resulting in intermittent or continuous high impedance. The lead-related condition may occur during implantation of lead 20 or after implantation of lead 20, as stresses are applied to 20 lead during movement of patient 14 and/or from regular movement of heart 12.

As another example, a lead-related condition may occur when an electrical connection between IMD 16 and an electrical contact of a lead becomes intermittently or continuously disrupted. For example, set screws may loosen, which may result in the lead gradually loosening from IMD 16. The disruption of the connection between the electrical contact of a lead and the IMD may result in an open circuit or a high impedance circuit.

Processor 80 may detect a loss of LV 32 capture using any suitable technique (122). In some examples, processor 80 determines whether an LV sensing event ($LV_S$) occurs within a particular time range of the delivery of the LV pacing pulse ($LV_P$). If the LV pacing pulse ($LV_P$) captured LV 32, the intrinsic depolarization of LV 32 is expected to occur within a predetermined range of time of the delivery of the LV pacing pulse ($LV_P$). In other examples, processor 80 detects loss of LV 32 capture based by checking the impedance of an electrical path including the electrodes of lead 20. In accordance with established techniques, processor 80 may detect a lead-related condition of the impedance exceeds a particular value or if the impedance changes over time at a particular rate.

If loss of LV capture is not detected (122), processor 80 continues sensing atrial events or delivering atrial pacing pulses (114) and controlling stimulation generator 84 (114) and deliver the LV pacing pulse ($LV_P$) to heart 12 upon expiration of the most recently determined $A_{P/S}$–$LV_P$ delay (116). If loss of LV capture is detected (122), processor 80 discontinues the pre-excitation fusion pacing therapy and, in some cases, switch pacing modes (124). Processor 80 may, for example, switch to a biventricular pacing mode.

In some examples, processor 80 may also generate a system integrity indication upon detecting loss of LV capture (122). The system integrity indication may be a value, flag or other signal generated by processor 80 and stored by memory 82 of IMD 16. In some examples, processor 80 may also transmit the system integrity indication to an external device, such as programmer 24 or a remote computing device, as described with respect to FIG. 11. The system integrity indication may be used for later analysis of therapy system 10 by a clinician or to generate an alert to patient 14 that therapy system 10 may need to be checked by a clinician. In some examples, processor 80 of IMD 16 or processor 100 of programmer 24 may recommend a corrective action upon alerting a clinician. For example, processor 80 may recommend that lead 20 (implanted with LV 32) be checked for a loose connection with connector block 34 of IMD 16.

Processor 80 may utilize the techniques shown in FIGS. 7 and 8 in conjunction with each other. For example, processor 80 may continue sensing atrial events or delivering atrial pacing pulses (114) and control stimulation generator 84 (114) and deliver the LV pacing pulse ($LV_P$) to heart 12 (116) until a loss of capture is detected (122) or upon expiration of a timer or a predetermined number of cardiac cycles (118).

Figure 9A:
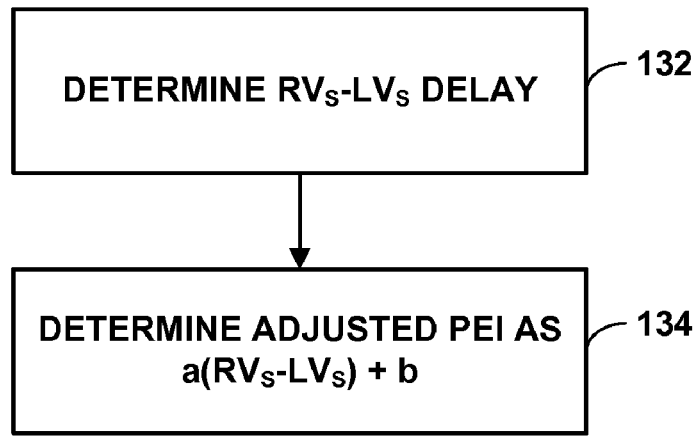
FIGS. 9A and 9B are flow diagrams of example techniques for determining an adjusted pre-excitation interval for the delivery of a pacing stimulus to a later depolarizing ventricle.

FIG. 9A is a flow diagram of an example technique for determined an adjusted PEI, which may be used to determine a pacing interval based on a LV sense event. Examples of pacing intervals include, for example, the $A_{P/S}$–$LV_P$ delay or the $LV_S$–$LV_P$ delay. After delivering a pacing stimulus to LV 32, processor 80 determines the interval of time between an RV sensing event ($RV_S$) and a subsequent LV sensing event ($LV_S$) (132). This may be referred to as the $RV_S$–$LV_S$ delay or the interventricular conduction delay. The interventricular conduction delay may indicate the extent to which the conduction dysfunction of heart 12 of patient 14 affects the filling of heart 12, e.g., because of the delay in the intrinsic conduction of LV 32. In the example shown in FIG. 9A, processor 80 determines the duration of the adjusted PEI as a function of the $RV_S$–$LV_S$ delay. In particular, in FIG. 9A, processor 80 determines the duration of the adjusted PEI in accordance with Equation (2) above, which is reproduced below:

$$\text{Adjusted PEI} = a(RV_S - LV_S) + b \qquad \text{Equation (2):}$$

The coefficients "a" and "b" in Equation (2) may be a fixed, empirical coefficient. In some examples, "a" is substantially equal to 1, and "b" may be substantially equal to PEI or less than PEI. However, in some examples, "b" may be greater than PEI. The $RV_S$–$LV_S$ delay may be determined while pacing therapy is not delivered to patient 12, such that the $RV_S$–$LV_S$ delay reflects the interventricular conduction delay of patient 12 when patient 12 does not receive pacing therapy.

In examples in which the coefficient "b" is based on the PEI, processor 80 determines PEI, e.g., based on data programmed into IMD 16 by a clinician. The PEI may be an interval of time prior to the intrinsic depolarization of the RV 28 that is required to pre-excite LV 32 in order to achieve fusion with the intrinsic conduction of RV 28. In some examples, a clinician may determine one or more appropriate PEI values for patient 14 with the aid of an echocardiograph, which may be used to evaluate the filling of heart 12 (e.g., the fill times). In such examples, the clinician evaluates echocardiographic images of LV filling as various PEI values are programmed. The PEI value at which left-ventricular filling looks best (e.g., both active and passive filling phases present and not truncated) may be selected by the clinician.

In other examples, a clinician may determine one or more appropriate PEI values with the aid of an ECG generated by external, electrodes. Various characteristics of the ECG may indicate when the conduction of LV 32 has fused with the conduction of RV 28. In some examples, the PEI value that results in equal amplitudes of the R-waves and Q-waves in an ECG sensed via a LV precordial lead may be considered to yield desirable fusion. In other examples the desirable PEI value may be determined to be a linear function of the P-R interval and QRS duration, e.g., PEI=h*PR+i*QRS+j, where "h", "i", and "j" are fixed coefficients.

Figure 9B:
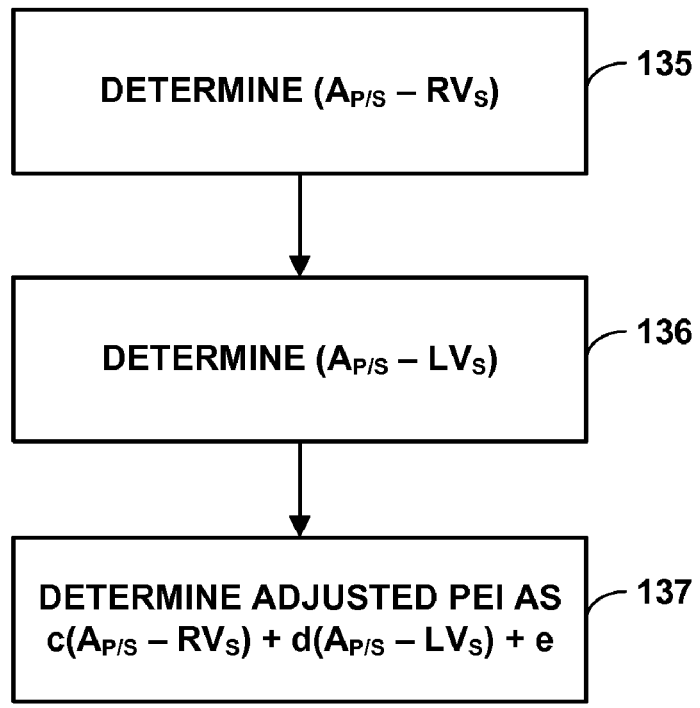

FIG. 9B is a flow diagram of another example technique for determined an adjusted PEI based on atrioventricular delays of heart 12 of patient 14. Processor 80 determines a time interval between an atrial pace or sensing event ($A_{P/S}$) and an RV sensing event ($RV_S$) (135). In addition, processor 80 determines a time interval between an atrial pace or sensing event ($A_{P/S}$) and an LV sensing event ($LV_S$) (136), which may be the LV sensing event for the same cardiac cycle in which the RV sensing event ($RV_S$) was detected. Processor 90 may then determine the adjusted PEI in accordance with Equation (4), which is reproduced below:

$$\text{Adjusted PEI}=c(A_{P/S}-RV_S)+d(A_{P/S}-LV_S)+e \quad \text{Equation (4):}$$

Figure 10:
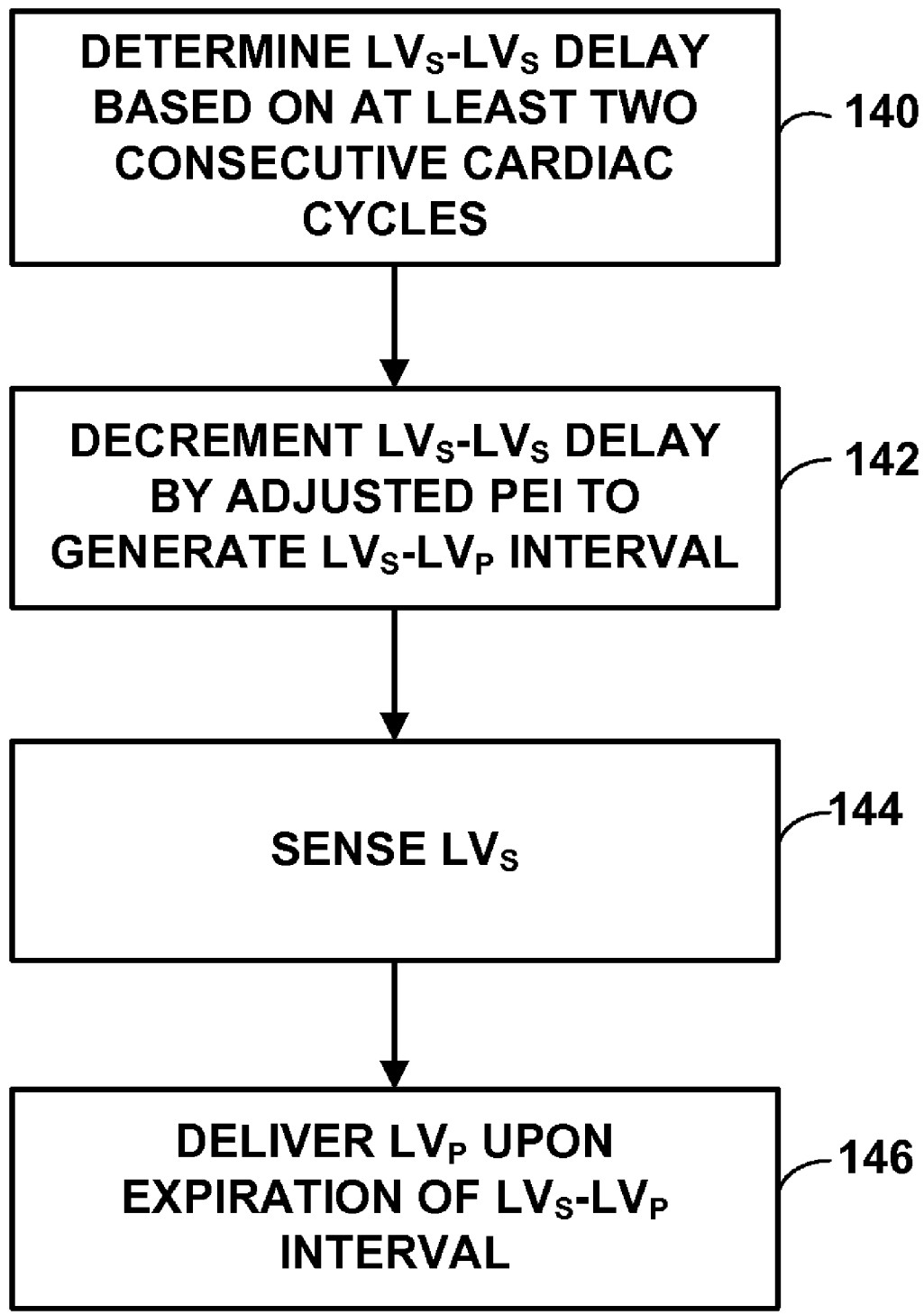
FIG. 10 is a flow diagram of an example technique for providing fusion-based cardiac resynchronization therapy.

FIG. 10 is a flow diagram of another example technique for providing fusion-based cardiac resynchronization therapy to patient 14. In the technique shown in FIG. 10, processor 80 (FIG. 4) of IMD 16 times the delivery of a pacing pulse to LV 32 (FIG. 2) relative to LV sensing event ($LV_S$). Processor 80 may implement the technique shown in FIG. 10 to determine an $LV_S$-$LV_P$ delay, which is one example of a pacing interval, for delivering the LV pacing stimulus to heart 12.

In accordance with the technique shown in FIG. 10, processor 80 determines an interval between LV sensing events of at least two consecutive cycles (140). In some examples, the interval, referred to as the $LV_S$-$LV_S$ interval, may be a mean or median $LV_S$-$LV_S$ interval for two or more cardiac cycles. Processor 80 may receive signals from sensing module 86 (FIG. 4) of IMD 16 in order to determine the $LV_S$-$LV_S$ interval. For example, processor 80 may receive LV event signals generated by sensing module 86 and determine the interval of time between subsequent LV event signals in order to determine the $LV_S$-$LV_S$ interval. Other techniques for determining the $LV_S$-$LV_S$ interval are contemplated.

Processor 80 decrements the determined $LV_S$-$LV_S$ interval by the adjusted PEI to general an $LV_S$-$LV_P$ interval (142). As discussed above with reference to FIG. 1, the $LV_S$-$LV_P$ interval is a pacing interval that indicates the interval of time following an LV sensing event (e.g., a sensed R-wave) at which processor 80 controls stimulation generator 84 to deliver an LV pacing pulse in order to provide efficacious fusion pacing of LV 32 with the intrinsic depolarization of RV 28. In order to provide pre-excitation fusion pacing therapy to patient 14, processor 80 may sense an LV event ($LV_S$) in a cardiac cycle that is after the first cardiac cycle (144) and deliver a pacing stimulus to LV 32 (LVP) upon expiration of the $LV_S$-$LV_P$ interval that begins when the LV event ($LV_S$) is detected (146).

In some examples, processor 80 senses an LV event ($LV_S$) (144) and controls stimulation generator 84 to deliver the LV pacing pulse ($LV_P$) to heart 12 in accordance with the determined $LV_S$-$LV_P$ delay (146) in this manner for a substantially indefinite period of time. In other examples, processor 80 controls stimulation generator 84 to deliver the LV pacing pulse ($LV_P$) to heart 12 in accordance with the determined $LV_S$-$LV_P$ delay for a limited period of time. For example, as described with respect to FIG. 7, after delivering LV pacing pulse ($LV_P$) to heart 12, processor 80 may determine whether a timer has expired or whether a predetermined number of cardiac cycles have occurred. If the timer has expired or the predetermined number of cardiac cycles have occurred, processor 80 may determine whether the pacing interval should be adjusted. For example, processor 80 may re-determine the $LV_S$-$LV_S$ interval and re-determine the $LV_S$-$LV_P$ delay for timing the LV pacing pulses ($LV_P$). On the other hand, if the timer has not expired and/or the predetermined number of cardiac cycles have not occurred, processor 80 may continue sense an LV event ($LV_S$) (144) and control stimulation generator 84 to deliver the LV pacing pulse ($LV_P$) to heart 12 in accordance with the most recently determined $LV_S$-$LV_P$ delay (146).

In some examples, processor 80 may also deliver LV pacing pulses ($LV_P$) in accordance with the technique shown in FIG. 10 until a loss of capture of LV is detected, as described with respect to FIG. 8.

Figure 11:
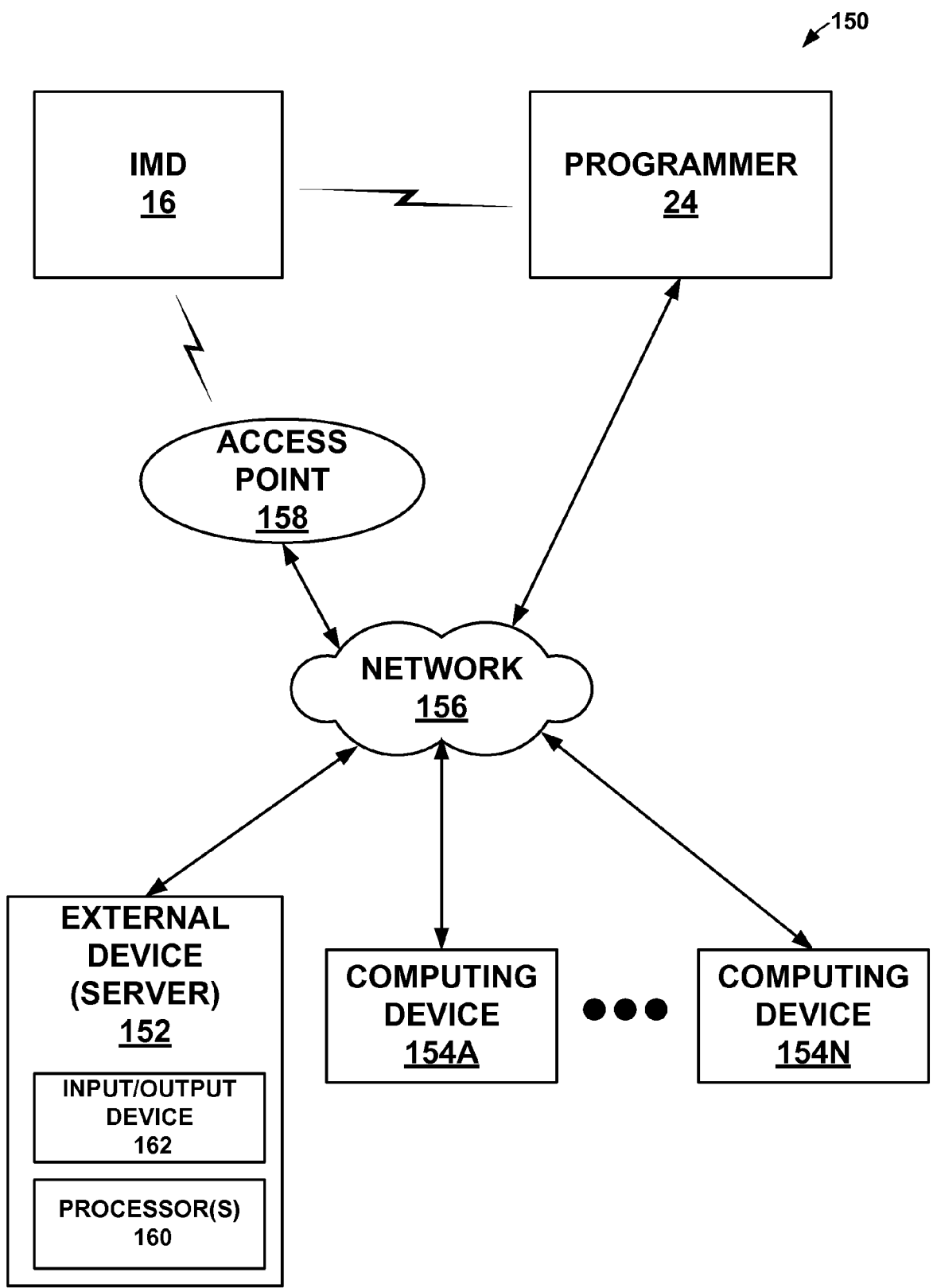
FIG. 11 is a block diagram illustrating an example system that includes an external device, such as a server, and one or more computing devices that are coupled to the IMD and programmer shown in FIG. 1 via a network.

FIG. 11 is a block diagram illustrating a system 150 that includes an external device 152, such as a server, and one or more computing devices 154A-154N that are coupled to IMD 16 and programmer 24 shown in FIG. 1 via a network 156, according to one example. In this example, IMD 16 uses its telemetry module 88 (FIG. 4) to communicate with programmer 24 via a first wireless connection, and to communicate with an access point 158 via a second wireless connection. In the example of FIG. 11, access point 158, programmer 24, external device 152, and computing devices 154A-154N are interconnected, and able to communicate with each other, through network 156. In some cases, one or more of access point 158, programmer 24, external device 152, and computing devices 154A-154N may be coupled to network 156 through one or more wireless connections. IMD 16, programmer 24, external device 152, and computing devices 154A-154N may each comprise one or more processors, such as one or more microprocessors, DSPs, ASICs, FPGAs, programmable logic circuitry, or the like, that may perform various functions and operations, such as those described herein.

Access point 158 may comprise a device that connects to network 156 via any of a variety of connections, such as telephone dial-up, digital subscriber line (DSL), or cable modem connections. In other examples, access point 158 may be coupled to network 156 through different forms of connections, including wired or wireless connections. In some examples, access point 158 may communicate with programmer 24 and/or IMD 16. Access point 158 may be co-located with patient 14 (e.g., within the same room or within the same site as patient 14) or may be remotely located from patient 14. For example, access point 158 may be a home monitor that is located in the patient's home or is portable for carrying with patient 14.

During operation, IMD 16 may collect, measure, and store various forms of diagnostic data. For example, as described previously, IMD 16 may collect ECG and/or EGM signals, different time intervals for timing the delivery of a pacing pulse to LV 32 (e.g., the $A_{P/S}$-$LV_P$ delay or the $LV_S$-$LV_P$ delay). In certain cases, IMD 16 may directly analyze collected diagnostic data and generate any corresponding reports or alerts. In some cases, however, IMD 16 may send diagnostic data to programmer 24, access point 158, and/or external device 152, either wirelessly or via access point 158 and network 156, for remote processing and analysis.

For example, IMD 16 may send programmer 24 data that indicates whether loss of capture of LV 32 was detected or a system integrity indication that was generated upon detection of the loss of LV capture. Programmer 24 may generate reports or alerts after analyzing the data and determining that there may be a possible condition with lead 20. As another example, IMD 16 may send the system integrity indication generated by processor 80 (FIG. 4) to programmer 24, which may take further steps to determine whether there may be a possible condition with one or more of leads 18, 20, and 22. For example, programmer 24 may initiate lead impedance tests or IMD 16 may provide lead impedance information, if such information is already available.

In another example, IMD 16 may provide external device 152 with collected EGM data, system integrity indications, and any other relevant physiological or system data via access point 158 and network 156. External device 152 includes one or more processors 160. In some cases, external device 152 may request such data, and in some cases, IMD 16 may automatically or periodically provide such data to external device 152. Upon receipt of the diagnostic data via input/output device 162, external device 152 is capable of analyzing the data and generating reports or alerts upon determination that there may be a possible condition with one or more of leads 18, 20, and 22 or with patient 14.

In one example, external device 152 may comprise a secure storage site for information that has been collected from IMD 16 and/or programmer 24. In this example, network 156 may comprise an Internet network, and trained professionals, such as clinicians, may use computing devices 154A-154N to securely access stored data on external device 152. For example, the trained professionals may need to enter usernames and passwords to access the stored information on external device 152. In one embodiment, external device 152 may be a CareLink server provided by Medtronic, Inc., of Minneapolis, Minn.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   detecting a ventricular sensing event of a ventricular chamber of a heart during at least a first cardiac cycle; and
   controlling a stimulation generator to deliver pre-excitation fusion pacing therapy to the ventricular chamber during a second cardiac cycle that follows the first cardiac cycle, wherein controlling the stimulation generator comprises controlling the stimulation generator to deliver the pre-excitation fusion pacing therapy based on a pacing interval that is determined based on a time interval between a pacing event or a sensing event of the heart and the ventricular sensing event decremented by an adjusted pre-excitation interval.

2. The method of claim 1, wherein detecting the ventricular sensing event comprises detecting an R-wave of an electrical cardiac signal sensed with at least one electrode implanted within the ventricular chamber.

3. The method of claim 1, wherein controlling the stimulation generator to deliver the pre-excitation fusion pacing comprises controlling the stimulation generator to deliver a single pacing pulse to the ventricular chamber.

4. The method of claim 1, further comprising:
   with a processor, determining the time interval, the time interval being between at least one of an atrial sensing event or an atrial pacing event for the at least the first cardiac cycle and the ventricular sensing event; and
   with the processor, determining the pacing interval based on the time interval.

5. The method of claim 4, wherein the atrial sensing event comprises a first atrial sensing event and the atrial pacing event comprises a first atrial pacing event, and delivering the pre-excitation fusion pacing therapy comprises:
   detecting at least one of a second atrial sensing event or a second atrial pacing event of the second cardiac cycle; and
   delivering the pre-excitation fusion pacing therapy upon expiration of the pacing interval that begins at detection of the at least one of the second atrial sensing event or the second atrial pacing event of the second cardiac cycle.

6. The method of claim 4, wherein pacing interval substantially equals the time interval decremented by the adjusted pre-excitation interval.

7. The method of claim 1, wherein the ventricular chamber comprises a first ventricular chamber, the ventricular sensing event comprises a first ventricular sensing event, and the time interval comprises a first time interval, the method further comprising determining the adjusted pre-excitation interval by at least:
   determining a second time interval between the first ventricular sensing event and a second ventricular sensing event sensed in a second ventricular chamber of the heart; and
   incrementing the second time interval by a predetermined pre-excitation interval.

8. The method of claim 1, wherein the ventricular chamber comprises a first ventricular chamber, the ventricular sensing event comprises a first ventricular sensing event, and the time interval comprises a first time interval, the method further comprising determining the adjusted pre-excitation interval by at least:
   determining a second time interval between the first ventricular sensing event and a second ventricular sensing event sensed in a second ventricular chamber of the heart; and determining the adjusted pre-excitation interval as a linear function of the second time interval.

9. The method of claim 1, wherein the ventricular chamber comprises a first ventricular chamber and the time interval comprises a first time interval, the method further comprising determining the adjusted pre-excitation interval by at least:
   determining a second time interval between the at least one of an atrial sensing event or an atrial pacing event for the at least the first cardiac cycle and a second ventricular sensing event sensed in a second ventricular chamber of the heart; and
   determining the adjusted pre-excitation interval as a linear function of the first time interval and the second time interval.

10. The method of claim 1, further comprising:
    determining the time interval, the time interval being between successive ventricular sensing events for the ventricular chamber; and
    determining the pacing interval based on the time interval.

11. The method of claim 10, further comprising detecting a second ventricular sensing event of the ventricular chamber during the second cardiac cycle, wherein delivering the pre-excitation fusion pacing therapy comprises delivering the pre-excitation fusion pacing therapy upon expiration of the pacing interval that begins at detection of the second ventricular sensing event.

12. The method of claim 10, wherein the pacing interval substantially equals the time interval decremented by the adjusted pre-excitation interval.

13. The method of claim 1, further comprising:
    determining whether at least one of a timer expired or a predetermined number of cardiac cycles have occurred; and
    with a processor, updating the pacing interval after the at least one of the timer expired or the predetermined number of cardiac cycles have occurred.

14. The method of claim 1, wherein delivering the pre-excitation fusion pacing therapy comprises delivering electrical stimulation to the ventricular chamber with an implantable medical lead, the method further comprising:
    detecting loss of capture of the ventricular chamber by the electrical stimulation; and
    delivering pacing therapy to the heart according to a pacing mode that is different than the pre-excitation fusion pacing therapy upon detecting the loss of capture.

15. The method of claim 1, wherein the ventricular chamber is a left ventricular chamber of the heart.

16. The method of claim 1, wherein the ventricular chamber is a right ventricular chamber of the heart.

17. The method of claim 1, wherein the ventricular chamber is a first ventricular chamber of the heart and the heart comprises a second ventricular chamber that activates before the first ventricular chamber during the first cardiac cycle.

18. A system comprising:
    a stimulation generator configured to deliver pre-excitation fusion pacing therapy to a ventricular chamber of a heart; and
    a processor configured to detect a ventricular sensing event of the ventricular chamber during at least a first cardiac cycle and control the stimulation generator to deliver the pre-excitation fusion pacing therapy to the ventricular chamber during a second cardiac cycle that follows the first cardiac cycle, wherein the processor is configured to control the stimulation generator to deliver the pre-excitation fusion pacing based on a pacing interval that is determined based on a time interval between a pacing event or a sensing event of the heart and the ventricular sensing event decremented by an adjusted pre-excitation interval.

19. The system of claim 18, further comprising a sensing module configured to monitor an electrical cardiac signal of the ventricular chamber via at least one electrode, wherein the processor is configured to detect the ventricular sensing event by at least detecting an R-wave of the electrical cardiac signal.

20. The system of claim 18, wherein the processor is configured to determine the time interval, the time interval being between at least one of an atrial sensing event or an atrial pacing event for the at least the first cardiac cycle and the ventricular sensing event.

21. The system of claim 20, wherein the atrial sensing event comprises a first atrial sensing event and the atrial pacing event comprises a first atrial pacing event, and wherein the processor is configured to control the stimulation generator to deliver the pre-excitation fusion pacing therapy by at least detecting at least one of a second atrial sensing event or a second atrial pacing event of the second cardiac cycle and controlling the stimulation generator to deliver the pre-excitation fusion pacing therapy upon expiration of the pacing interval that begins at detection of the at least one of the second atrial sensing event or the second atrial pacing event of the second cardiac cycle.

22. The system of claim 18, wherein pacing interval substantially equals the time interval decremented by the adjusted pre-excitation interval.

23. The system of claim 18, wherein the ventricular chamber comprises a first ventricular chamber, the ventricular sensing event comprises a first ventricular sensing event, and the time interval comprises a first time interval, and wherein the processor is configured to determine the adjusted pre-excitation interval by at least:
    determining a second time interval between the first ventricular sensing event and a second ventricular sensing event sensed in a second ventricular chamber of the heart; and
    incrementing the second time interval by a predetermined pre-excitation interval.

24. The system of claim 18, wherein the ventricular chamber comprises a first ventricular chamber, the ventricular sensing event comprises a first ventricular sensing event, and the time interval comprises a first time interval, and wherein the processor is configured to determine the adjusted pre-excitation interval by at least:
    determining a second time interval between the first ventricular sensing event and a second ventricular sensing event sensed in a second ventricular chamber of the heart; and
    determining the adjusted pre-excitation interval as a linear function of the second time interval.

25. The system of claim 18, wherein the ventricular chamber comprises a first ventricular chamber, the ventricular sensing event comprises a first ventricular sensing event, and the time interval comprises a first time interval, and wherein the processor is configured to determine the adjusted pre-excitation interval by at least:
    determining a second time interval between the at least one of an atrial sensing event or an atrial pacing event for the at least the first cardiac cycle and a second ventricular sensing event sensed in a second ventricular chamber of the heart; and
    determining the adjusted pre-excitation interval as a linear function of the first time interval and the second time interval.

26. The system of claim 18, wherein the processor is configured to determine the time interval, the time interval being between successive ventricular sensing events for the ventricular chamber.

27. The system of claim 26, wherein the processor is configured to detect a second ventricular sensing event of the ventricular chamber during the second cardiac cycle, and control the stimulation generator to deliver the pre-excitation fusion pacing therapy upon expiration of the pacing interval that begins at detection of the second ventricular sensing event.

28. The system of claim 27, wherein the pacing interval substantially equals the time interval decremented by the adjusted pre-excitation interval.

29. The system of claim 18, wherein the processor is configured to determine whether at least one of a timer expired or a predetermined number of cardiac cycles have occurred, and update the pacing interval after the at least one of the timer expired or the predetermined number of cardiac cycles have occurred.

30. The system of claim 18, wherein the processor is configured to control the stimulation generator to deliver the pre-excitation fusion pacing therapy to the ventricular chamber with an implantable medical lead, and wherein the processor is configured to detect loss of capture of the ventricular chamber by the electrical stimulation, and control the stimulation generator to deliver pacing therapy to the heart according to a pacing mode that is different than the pre-excitation fusion pacing therapy upon detecting the loss of capture of the ventricular chamber.

31. The system of claim 18, wherein the ventricular sensing event comprises a first ventricular sensing event, the pacing event comprises an atrial pacing event of the first cardiac cycle and the sensing event comprises an atrial sensing event of the first cardiac cycle or a second ventricular sensing event of the ventricular chamber for a third cardiac cycle, wherein the second cardiac cycle follows the third cardiac cycle.

32. A system comprising:
   means for detecting a ventricular sensing event of a ventricular chamber of a heart during at least a first cardiac cycle;
   means for delivering pre-excitation fusion pacing therapy to the ventricular chamber during a second cardiac cycle that follows the first cardiac cycle; and
   means for controlling the means for delivering pre-excitation fusion pacing therapy to deliver the pacing therapy based on a pacing interval that is determined based on a time interval between a pace event or a sense event of the heart and the ventricular sensing event decremented by an adjusted pre-excitation interval.

33. The system of claim 32, further comprising:
   means for determining the time interval, the time interval being between at least one of a first atrial sensing event or a first atrial pacing event for the at least the first cardiac cycle and the ventricular sensing event;
   means for determining the pacing interval based on the time interval;
   means for detecting at least one of a second atrial sensing event or a second atrial pacing event of the second cardiac cycle,
   wherein the means for controlling is configured to control the means for delivering pre-excitation fusion pacing therapy to deliver the pre-excitation fusion pacing therapy upon expiration of the pacing interval that begins at detection of the at least one of the second atrial sensing event or the second atrial pacing event.

34. The system of claim 33, further comprising:
   means for determining the time interval, the time interval being between successive ventricular sensing events for the ventricular chamber; and
   means for determining the pacing interval based on the time interval.

35. The system of claim 34, wherein the ventricular sensing event comprises a first ventricular sensing event, system further comprising means for detecting a second ventricular sensing event of the ventricular chamber during the second cardiac cycle, wherein the means for controlling is configured to control the means for delivering pre-excitation fusion pacing therapy to deliver the pre-excitation fusion pacing therapy upon expiration of the pacing interval that begins at detection of the second ventricular sensing event.

36. A computer-readable medium comprising instructions that, when executed by a programmable processor, cause the programmable processor to:
   detect a ventricular sensing event of a ventricular chamber of a heart during at least a first cardiac cycle; and
   control a stimulation generator to deliver pre-excitation fusion pacing therapy to the ventricular chamber during a second cardiac cycle that follows the first cardiac cycle, wherein the instructions cause the programmable processor to control the stimulation generator to deliver the pre-excitation fusion pacing therapy based on a pacing interval that is determined based on a time interval between a pacing event or a sensing event of the heart and the ventricular sensing event decremented by an adjusted pre-excitation interval.

37. The computer-readable medium of claim 36, further comprising instructions that, when executed by the programmable processor, cause the programmable processor to:
   determine the time interval, the time interval being between at least one of an atrial sensing event or an atrial pacing event for the at least the first cardiac cycle and the ventricular sensing event; and
   determine the pacing interval based on the time interval.

38. The computer-readable medium of claim 36, further comprising instructions that, when executed by the programmable processor, cause the programmable processor to:
   determine the time interval, the time interval being between successive ventricular sensing events for the ventricular chamber; and
   determine the pacing interval based on the time interval.

39. A system comprising:
   a stimulation generator configured to deliver pre-excitation fusion pacing therapy to a ventricular chamber of a heart; and
   a processor configured to detect a ventricular sensing event of the ventricular chamber during a first cardiac cycle and control the stimulation generator to deliver the pre-excitation fusion pacing therapy to the ventricular chamber during a second cardiac cycle that follows the first cardiac cycle, wherein the processor is configured to control the stimulation generator to deliver the pre-excitation fusion pacing therapy based on a pacing interval that is determined based on a first time interval between at least one of an atrial pacing event or an atrial sensing event for the first cardiac cycle and the ventricular sensing event, or based on a second time interval between successive ventricular sensing events for the ventricular chamber.

40. The system of claim 39, wherein the atrial sensing event comprises a first atrial sensing event and the atrial pacing event comprises a first atrial pacing event, and the pacing interval is determined based on the first time interval, wherein the processor is configured to control the stimulation generator to deliver the pre-excitation fusion pacing therapy by at least detecting at least one of a second atrial sensing event or a second atrial pacing event of the second cardiac cycle and controlling the stimulation generator to deliver the pre-excitation fusion pacing therapy upon expiration of the pacing interval that begins at detection of the at least one of the second atrial sensing event or the second atrial pacing event of the second cardiac cycle.

41. The system of claim 39, the pacing interval is determined based on the second time interval, wherein the processor is configured to control the stimulation generator to deliver the pre-excitation fusion pacing therapy by at least detecting a second ventricular sensing event of the ventricular chamber during the second cardiac cycle, and controlling the stimulation generator to deliver the pre-excitation fusion pacing therapy upon expiration of the pacing interval that begins at detection of the second ventricular sensing event.

42. The system of claim 39, wherein pacing interval substantially equals the first time interval or the second time interval decremented by an adjusted pre-excitation interval.

* * * * *